United States Patent
Koizumi et al.

(10) Patent No.: US 8,573,776 B2
(45) Date of Patent: Nov. 5, 2013

(54) FUNDUS OBSERVATION APPARATUS

(75) Inventors: Hiroshi Koizumi, Tokyo (JP); Koki Harumoto, Tokyo (JP); Tsutomu Kikawa, Tokyo (JP); Takefumi Hayashi, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 82 days.

(21) Appl. No.: 13/264,117

(22) PCT Filed: Apr. 2, 2010

(86) PCT No.: PCT/JP2010/002424
§ 371 (c)(1),
(2), (4) Date: Oct. 12, 2011

(87) PCT Pub. No.: WO2010/119632
PCT Pub. Date: Oct. 21, 2010

(65) Prior Publication Data
US 2012/0033181 A1 Feb. 9, 2012

(30) Foreign Application Priority Data

Apr. 15, 2009 (JP) ................................ 2009-099447
Sep. 28, 2009 (JP) ................................ 2009-223312

(51) Int. Cl.
*A61B 3/14* (2006.01)
*A61B 3/15* (2006.01)
*A61B 3/12* (2006.01)

(52) U.S. Cl.
CPC .............. *A61B 3/152* (2013.01); *A61B 3/1225* (2013.01); *A61B 3/14* (2013.01)
USPC .......................................... 351/208; 351/206

(58) Field of Classification Search
USPC ....................................................... 351/208
See application file for complete search history.

(56) References Cited

U.S. PATENT DOCUMENTS 6,377,349 B1  4/2002 Fercher
2003/0199769 A1 10/2003 Podoleanu et al.
(Continued)

FOREIGN PATENT DOCUMENTS

EP  1 775 545 A2  4/2007
JP  09-276232 A  10/1997
(Continued)

OTHER PUBLICATIONS

Hammer, D.X. et al. Image stabilization for scanning laser ophthalmoscopy. Dec. 30, 2001; vol. 10, No. 26; IN: Optics Express; pp. 1542-1549.

(Continued)

*Primary Examiner* — Ricky Mack
*Assistant Examiner* — William Alexander
(74) *Attorney, Agent, or Firm* — Pearne & Gordon LLP

(57) ABSTRACT

The fundus observation apparatus 1 has a function to form tomographic images and 3-dimensional images of a fundus Ef by scanning signal light LS as well as a function to form a moving image (observation image K) of a fundus Ef during OCT measurement. Furthermore, the fundus observation apparatus 1 includes an x-correction part 231 and a y-correction part 232 for correcting a position in the fundus surface direction of the 3-dimensional image based on the observation image K, and a z-correction part 233 for correcting the position in the fundus depth direction of a 3-dimensional image, based on a tomographic image Gi of the fundus Ef based on the detection results of interference light LC of separately scanned signal light LS and reference light LR.

26 Claims, 14 Drawing Sheets

(56) References Cited

U.S. PATENT DOCUMENTS

| | | |
|---|---|---|
| 2006/0100528 A1 | 5/2006 | Chan et al. |
| 2007/0222945 A1* | 9/2007 | Tsukada et al. ............... 351/205 |
| 2007/0222946 A1* | 9/2007 | Fukuma et al. ............... 351/206 |
| 2007/0236661 A1* | 10/2007 | Fukuma et al. ............... 351/205 |
| 2008/0151256 A1 | 6/2008 | Kikawa et al. |
| 2010/0039616 A1 | 2/2010 | Yumikake et al. |

FOREIGN PATENT DOCUMENTS

| | | |
|---|---|---|
| JP | 11-325849 A | 11/1999 |
| JP | 2002-139421 A | 5/2002 |
| JP | 2006-153838 A | 6/2006 |
| JP | 2006-212153 A | 8/2006 |
| JP | 2007-024677 A | 2/2007 |
| JP | 2007-130403 A | 5/2007 |
| JP | 2008-039651 A | 2/2008 |
| JP | 2008-073099 A | 4/2008 |
| JP | 2008-154939 A | 7/2008 |
| JP | 2008-267892 A | 11/2008 |

OTHER PUBLICATIONS

International Search Report for PCT/JP2010/002424; Apr. 27, 2010.
Extended European Search Report for Application No. 10764219.1-1660/2420181 dated Jul. 5, 2013.

* cited by examiner

FUNDUS OBSERVATION APPARATUS

TECHNICAL FIELD

The present invention relates to a fundus observation apparatus configured to form images of a fundus of an eye by using optical coherence tomography.

BACKGROUND ART

In recent years, optical coherence tomography that forms images of the surface morphology and internal morphology of an object by using a light beam from a laser light source or the like has attracted attention. Unlike an X-ray CT apparatus, optical coherence tomography is noninvasive to human bodies, and is therefore expected to be utilized in the medical field and biological field.

Patent Document 1 discloses a device to which optical coherence tomography is applied. This device has such a configuration that: a measuring arm scans an object by a rotary deflection mirror (a Galvano mirror); a reference arm is provided with a reference mirror; and an interferometer is mounted at the outlet to analyze, by a spectrometer, the intensity of an interference light of light fluxes from the measurement arm and the reference arm. Moreover, the reference arm is configured to gradually change the light flux phase of the reference light by discontinuous values.

The device of Patent Document 1 uses a technique of so-called "Fourier Domain OCT (Optical Coherence Tomography)." That is to say, the device radiates a low coherence light beam to an object, superposes the reflected light and the reference light to generate an interference light, and acquires the spectral intensity distribution of the interference light to execute Fourier transform, thereby imaging the morphology in the depth direction (the z-direction) of the object. The technique of this type is also called Spectral Domain.

Furthermore, the device described in Patent Document 1 is provided with a Galvano mirror that scans with a light beam (a signal light), and is thereby configured to form an image of a desired measurement target region of the object. Because this device is configured to scan with the light beam only in one direction (the x-direction) orthogonal to the z-direction, an image formed by this device is a two-dimensional tomographic image in the depth direction (the z-direction) along the scanning direction (the x-direction) of the light beam.

Patent Document 2 discloses a technique of scanning with a signal light in the horizontal direction (x-direction) and the vertical direction (y-direction) to form a plurality of two-dimensional tomographic images in the horizontal direction, and acquiring and imaging three-dimensional tomographic information of a measured range based on the tomographic images. As the three-dimensional imaging, for example, a method of arranging and displaying a plurality of tomographic images in the vertical direction (referred to as stack data or the like), and a method of executing a rendering process on a plurality of tomographic images to form a three-dimensional image are considered.

Patent Documents 3 and 4 disclose other types of OCT devices. Patent Document 3 describes an OCT device that images the morphology of an object by scanning the object with light of various wavelengths, acquiring the spectral intensity distribution based on an interference light obtained by superposing the reflected lights of the light of the respective wavelengths on the reference light, and executing Fourier transform. Such an OCT device is called a Swept Source type or the like. The Swept Source type is a kind of the Fourier Domain type.

Further, Patent Document 4 describes an OCT device that radiates a light having a predetermined beam diameter to an object and analyzes the components of an interference light obtained by superposing the reflected light and the reference light, thereby forming an image of the object in a cross-section orthogonal to the travelling direction of the light. Such an OCT device is called a full-field type, en-face type or the like.

Patent Document 5 discloses a configuration in which the OCT is applied to the ophthalmologic field. According to this fundus observation apparatus, it is possible to obtain tomographic images and 3-dimensional images of a fundus. Before the OCT device was applied to the ophthalmologic field, a fundus observation apparatus such as a retinal camera had been used (for example, refer to Patent Document 6).

Compared to a retinal camera that can only photograph a fundus from the front, a fundus observation apparatus using OCT has a merit that tomographic images and 3-dimensional images of a fundus are obtained. Therefore, contribution to increase of the diagnosis accuracy and early detection of a lesion are expected.

PRIOR ART DOCUMENTS

Patent Documents

[Patent Document 1]
Japanese Unexamined Patent Application Publication No. Hei 11-325849
[Patent Document 2]
Japanese Unexamined Patent Application Publication No. 2002-139421
[Patent Document 3]
Japanese Unexamined Patent Application Publication No. 2007-24677
[Patent Document 4]
Japanese Unexamined Patent Application Publication No. 2006-153838
[Patent Document 5]
Japanese Unexamined Patent Application Publication No. 2008-73099
[Patent Document 6]
Japanese Unexamined Patent Application Publication No. Hei 9-276232

DISCLOSURE OF THE INVENTION

Problem that the Invention is to Solve

For capturing a 3-dimensional image of a fundus, measurement is conducted by two-dimensional scanning with a signal light. This scanning requires approximately a few seconds. Consequently, there is a risk of the eye moving (fixation misalignment, etc.) or blinking during scanning. If this occurs, the 3-dimensional image may be distorted or a part of the image in the region subject to measurement may not be able to be obtained; thereby, deteriorating the accuracy of the image.

This invention resolves the abovementioned problem, with the purpose of providing a fundus observation apparatus capable of capturing a highly accurate OCT image, even if the eye moves or blinks during scanning with a signal light.

Means for Solving the Problem

In order to achieve the aforementioned objects, an invention according to claim 1 is a fundus observation apparatus comprising: an optical system that splits low coherence light into signal light and reference light, generates interference light by superposing said signal light that has passed through the fundus of an eye and reference light that has passed through a reference optical path, and detects the generated interference light; a scanning part that sequentially irradiates said signal light to a plurality of scanning points by scanning said fundus with said signal light and; an image forming part that forms 1-dimensional images extending depthwise of said fundus at each of said plurality of scanning points based on the detection results of said interference light by said optical system; a detection part that detects the position of said fundus at a prescribed time interval when scanning with said signal light; and a calculation part that calculates the positional misalignment amount of said plurality of 1-dimensional images in the fundus surface direction, based on temporal changes of said detected position of said fundus.

Further, an invention according to claim 2 is the fundus observation apparatus according to claim 1, wherein said prescribed time interval is a substantially integral multiple of a scan time interval that is from the timing at which said signal light is irradiated to one of said plurality of scanning points to the timing at which said signal light is irradiated to the next scanning point; while said signal light is sequentially irradiated to said plurality of scanning points by said scanning part, said detection part detects the position of said fundus each time when the relevant integral number of scanning points are scanned; and said calculation part divides said plurality of 1-dimensional images into 1-dimensional image groups, each group comprising the relevant integral number of 1-dimensional images, specifies the position of each 1-dimensional image group based on the detection results of the position of said fundus when the relevant integral number of scanning points corresponding to each 1-dimensional image group are being scanned, and calculates said positional misalignment amount based on said specified position of each 1-dimensional image group.

Further, an invention according to claim 3 is the fundus observation apparatus according to claim 2, wherein said integral is one; said 1-dimensional image group consists of one 1-dimensional image; and said calculation part specifies the position of the 1-dimensional image with regard to said plurality of 1-dimensional images based on the detection results of the position of said fundus when a scanning point corresponding to the 1-dimensional image is being scanned, and calculates said positional misalignment amount based on the specified plurality of positions.

Further, an invention according to claim 4 is the fundus observation apparatus according to claim 2, wherein said integral is equal to or greater than two; said 1-dimensional image group consists of two or more 1-dimensional images; and said calculation part estimates, based on the detection results of the position of said fundus when two or more scanning points corresponding to one of said plurality of 1-dimensional image groups are being scanned and the detection results of the position of said fundus when two or more scanning points corresponding to the next 1-dimensional image group are being scanned, said positional misalignment amount of a 1-dimensional image included in said one of said plurality of 1-dimensional image group and/or said next 1-dimensional image group.

Further, an invention according to claim 5 is the fundus observation apparatus according to claim 1, wherein said detection part includes an imaging part that forms a moving image by imaging said fundus at said prescribed time interval when the scanning with said signal light is executed by said scanning part, and an image region-specifying part that specifies an image region of a characteristic site of said fundus in each still image forming said moving image, and obtains the position of said image region in said each still image as the position of said fundus.

Further, an invention according to claim 6 is the fundus observation apparatus according to claim 5, wherein said calculation part includes a scanning point-specifying part that, when there is a still image in which said image region is not specified by said image region-specifying part, specifies a scanning point of a 1-dimensional image corresponding to the still image; said scanning part reirradiates said signal light to the specified scanning point; and said image forming part forms a new 1-dimensional image based on the detection results of interference light of said reirradiated signal light and said reference light.

Further, an invention according to claim 7 is the fundus observation apparatus according to claim 1, wherein said calculation part includes a first correction part that corrects the position of said plurality of 1-dimensional images in the fundus surface direction, based on said calculated positional misalignment amount.

Further, an invention according to claim 8 is the fundus observation apparatus according to claim 1, wherein said calculation part sequentially calculates said positional misalignment amount based on the position of said fundus that is sequentially detected at said prescribed time interval when scanning with said signal light is executed; and comprising a controlling part that corrects the irradiation position of said signal light to said fundus by controlling said scanning part based on said sequentially calculated positional misalignment amount.

Further, an invention according to claim 9 is the fundus observation apparatus according to claim 1, wherein, said plurality of scanning points are arranged along a prescribed scanning line; said scanning part repeatedly scans along said prescribed scanning line with said signal light; said image forming part repeatedly forms said plurality of 1-dimensional images corresponding to said plurality of scanning points following the repetitive scanning; said calculation part repeatedly calculates said positional misalignment amount following the repetitive formations; comprising: a determination part which determines whether or not the repeatedly calculated each positional misalignment amount is included in a prescribed permissible range; and an image overlapping part that overlaps, for each 1-dimensional image corresponding to each scanning point, a set of said plurality of 1-dimensional images corresponding to said positional misalignment amount determined as inclusive to said prescribed permissible range; and said image forming part forms a tomographic image along said prescribed scanning line by arranging a plurality of new 1-dimensional images formed as a result of said overlapping in accordance with the arrangement of said plurality of scanning points.

Further, an invention according to claim 10 is the fundus observation apparatus according to claim 1, wherein said calculation part includes an image specifying part that specifies a 1-dimensional image with the calculated positional misalignment amount of greater than a prescribed value; said scanning part reirradiates said signal light towards a scanning point corresponding to each 1-dimensional image specified by said image specifying part; and said image forming part forms a new 1-dimensional image at the scanning point based on the detection results of interference light of said reirradiated signal light and said reference light.

Further, an invention according to claim 11 is the fundus observation apparatus according to claim 1, wherein said plurality of scanning points are arranged along a prescribed scanning line; said calculation part includes an image selecting part that, for each of said plurality of scanning points, selects the 1-dimensional image closest to the original position of the scanning point among said plurality of 1-dimensional images, based on the calculated positional misalignment amount; and said image forming part forms a tomographic image along said prescribed scanning line by arranging the selected 1-dimensional image in accordance with the arrangement of said plurality of scanning points.

Further, an invention according to claim 12 is the fundus observation apparatus according to claim 1, wherein said calculation part calculates the positional misalignment amount of said plurality of 1-dimensional images in the depth direction of said fundus, based on a separate 1-dimensional image group arranged in a separate scanning direction that is formed by said image forming part based on the detection results of interference light of signal light that is separately scanned by said scanning part and reference light.

Further, an invention according to claim 13 is the fundus observation apparatus according to claim 12, wherein said scanning part sequentially irradiates said signal light, as said separate scanning, to a prescribed number of scanning points along a scanning line crossing the arrangement direction of said plurality of scanning points; said image forming part forms said 1-dimensional image at each of said prescribed number of scanning points and forms a tomographic image corresponding to said scanning line based on said prescribed number of formed 1-dimensional images; and said calculation part specifies an image region of a characteristic layer of said fundus in said tomographic image, specifies the image region of said characteristic layer in a tomographic image formed by arranging said plurality of scanning points, calculates the depthwise displacement of said image region corresponding to said scanning line and said image region corresponding to said plurality of scanning points, and calculates the depthwise positional misalignment amount of said plurality of 1-dimensional images based on the calculated displacement.

Further, an invention according to claim 14 is the fundus observation apparatus according to claim 12, wherein said calculation part includes a second correction part that corrects the position of said plurality of 1-dimensional images in the depth direction, based on the calculated depthwise positional misalignment amount.

Further, an invention according to claim 15 is a fundus observation apparatus comprising: an optical system that splits low coherence light into signal light and reference light, generates interference light by superposing said signal light that has passed through the fundus of an eye and reference light that has passed through a reference optical path, and detects the generated interference light; a scanning part that two-dimensionally scans said fundus with said signal light; an image forming part that forms, based on the detection results of said interference light, a 3-dimensional image corresponding to the region of said fundus in which the two-dimensional scanning with said signal light is executed; an imaging part that forms a moving image of said fundus when the two-dimensional scanning with said signal light is executed; and a correction part that corrects the position of said 3-dimensional image in a fundus surface direction based on the formed moving image, and corrects the position of said 3-dimensional image in a fundus depth direction, based on a tomographic image of said fundus that is formed by said image forming part based on the detection results of interference light of separately scanned signal light by said scanning part and reference light.

Further, an invention according to claim 16 is the fundus observation apparatus according to claim 15, wherein said scanning part scans with said signal light along each of a plurality of scanning lines that are parallel to each other, as said two-dimensional scanning; said image forming part forms a tomographic image corresponding to each of said plurality scanning lines and forms said 3-dimensional image based on the formed plurality of tomographic images; said imaging part forms said moving image by forming still images when the scanning with said signal light is executed along each of said plurality of scanning lines; and said correction part specifies an image region of a characteristic site of said fundus in each of said plurality of still images, calculates the positional misalignment amount of said image region in said plurality of still images, and corrects the position of said 3-dimensional image in the fundus surface direction by correcting the relative position of said plurality of tomographic images based on the calculated positional misalignment amount.

Further, an invention according to claim 17 is the fundus observation apparatus according to claim 16, wherein said correction part calculates an interval of said plurality of tomographic images after said relative position is corrected; and said image forming part forms a plurality of tomographic images arranged at equal intervals based on the calculated interval as well as said plurality of tomographic images, and forms a 3-dimensional image based on the tomographic images formed at equal intervals.

Further, an invention according to claim 18 is the fundus observation apparatus according to claim 15, wherein said scanning part scans with said signal light along each of a plurality of scanning lines that are parallel to each other, as the two-dimensional scanning; said image forming part forms a tomographic image corresponding to each of said plurality of scanning lines and forms said 3-dimensional image based on the formed plurality of tomographic images; said imaging part forms said moving image by forming a still image when the scanning with said signal light is executed along each of said plurality of scanning lines; said correction part specifies an image region of a characteristic site of said fundus in each of said plurality of still images, calculates the positional misalignment amount in said image region in said plurality of still images, and determines whether or not the calculated positional misalignment amount is equal to or greater than a prescribed value; when determined that said positional misalignment amount is equal to or greater than the prescribed value, said scanning part rescans with said signal light along a scanning line located to a close region of a scanning line of a tomographic image corresponding to the still image whose positional misalignment amount is determined to be equal to or greater than the prescribed value; and said image forming part forms a new tomographic image based on the detection results of interference light of the rescanned signal light and the reference light, and forms a 3-dimensional image corresponding to said close region based on said new tomographic image.

Further, an invention according to claim 19 is the fundus observation apparatus according to claim 18, wherein said image forming part forms said 3-dimensional image based on a tomographic image corresponding to said still image whose positional misalignment amount is determined to be less than the prescribed value and said new tomographic image.

Further, an invention according to claim 20 is the fundus observation apparatus according to claim 15, wherein said scanning part scans with said signal light along each of a plurality of scanning lines that are parallel to each other, as said two-dimensional scanning; said image forming part forms a tomographic image corresponding to each of said plurality of scanning lines and forms said 3-dimensional image based on the formed plurality of tomographic images; said imaging part forms said moving image by forming a still image when said the scanning with the signal light is executed along each of said plurality of scanning lines; said correction part specifies an image region of a characteristic site of said fundus in each of said plurality of still images, calculates the positional misalignment amount of said image region in said plurality of still images, and selects, for each of said plurality of scanning lines, a tomographic image closest to the original position of the scanning line among said plurality of tomographic images based on the calculated positional misalignment amount; and said image forming part forms said 3-dimensional image based on the selected tomographic image.

Further, an invention according to claim 21 is the fundus observation apparatus according to claim 16, wherein when there exists said still image in which the image region of said characteristic site is not specified, said correction part specifies a scanning line of a tomographic image corresponding to the still image; said scanning part rescans with said signal light along the specified scanning line; and said image forming part forms a new tomographic image based on the detection results of interference light of the rescanned signal light and the reference light, and forms a 3-dimensional image of a region corresponding to the scanning line based on said new tomographic image.

Further, an invention according to claim 22 is the fundus observation apparatus according to claim 18, wherein when there exists said still image in which the image region of said characteristic site is not specified, said correction part specifies a scanning line of a tomographic image corresponding to the still image; said scanning part rescans with said signal light along the specified scanning line; and said image forming part forms a new tomographic image based on the detection results of interference light of the rescanned signal light and the reference light, and forms a 3-dimensional image of a region corresponding to the scanning line based on said new tomographic image.

Further, an invention according to claim 23 is the fundus observation apparatus according to claim 20, wherein when there exists said still image in which the image region of said characteristic site is not specified, said correction part specifies a scanning line of a tomographic image corresponding to the still image, said scanning part rescans with said signal light along the specified scanning line, and said image forming part forms a new tomographic image based on the detection results of interference light of the rescanned signal light and the reference light, and forms a 3-dimensional image of a region corresponding to the scanning line based on said new tomographic image.

Further, an invention according to claim 24 is the fundus observation apparatus according to claim 16, wherein said image forming part forms a 3-dimensional image of said fundus based only on the center portion excluding an image region in the tomographic image corresponding to a prescribed end part region in each of said plurality of scanning lines.

Further, an invention according to claim 25 is the fundus observation apparatus according to claim 18, wherein said image forming part forms a 3-dimensional image of said fundus based only on the center portion excluding an image region in the tomographic image corresponding to a prescribed end part region in each of said plurality of scanning lines.

Further, an invention according to claim 26 is the fundus observation apparatus according to claim 20, wherein said image forming part forms a 3-dimensional image of said fundus based only on the center portion excluding an image region in the tomographic image corresponding to a prescribed end part region in each of said plurality of scanning lines.

Further, an invention according to claim 27 is the fundus observation apparatus according to claim 15, wherein said scanning part scans with said signal light, as said separate scanning, along each of a prescribed number of scanning lines for correction crossing said plurality of scanning lines, said image forming part forms a tomographic image for correction corresponding to each of said scanning lines for correction, and said correction part specifies an image region of a characteristic layer of said fundus in said prescribed number of formed tomographic images for correction, and corrects the position of said 3-dimensional image in the fundus depth position by moving each of said plurality of tomographic images in the fundus depth position so as to match the depthwise position of the specified image region and the depthwise position of said image region of the characteristic layer in each of said plurality of tomographic images.

Effect of the Invention

According to the fundus observation apparatus related to the present invention, the positional misalignment amount of a plurality of 1-dimensional images in the fundus surface direction may be calculated, based on detected temporal changes in the position of the fundus by detecting the position of the fundus at a prescribed time interval during scanning with a signal light. By correcting the position of the plurality of 1-dimensional images, based on the positional misalignment amount, even if the eye moves or blinks during scanning with the signal light, it is possible to capture highly accurate OCT images.

Furthermore, according to the fundus observation apparatus related to the present invention, because the position in the fundus surface direction in a 3-dimensional image of a fundus may be corrected based on a moving image of the fundus and, because the depthwise position of the fundus of a 3-dimensional image may be corrected based on tomographic images of the fundus based on the detection results of interference light of the signal light that is separately scanned by a scanning part and reference light, even if the eye moves or blinks during scanning with the signal light, it is possible to capture a highly accurate 3-dimensional image (OCT image).

MODE FOR CARRYING OUT THE INVENTION

An example of an embodiment of a fundus observation apparatus according to the present invention will be described in detail with reference to the drawings.

The fundus observation apparatus according to the present invention forms tomographic images of a fundus using optical coherence tomography. Optical coherence tomography of an arbitrary type involving scanning with a signal light such as a Fourier Domain type, a swept source type, etc. are applicable to the fundus observation apparatus. It should be noted that an image obtained by optical coherence tomography is sometimes referred to as an OCT image. Furthermore, a measuring action for forming an OCT image is sometimes referred to as an OCT measurement.

In the following embodiments, a configuration to which a Fourier-Domain-type is applied will be described in detail. To be specific, in these embodiments, similar to a device disclosed in the Patent Document 5, a fundus observation apparatus that is capable of obtaining both tomographic images and photographed image of a fundus will be picked up.

First Embodiment

Configuration

Figure 1:
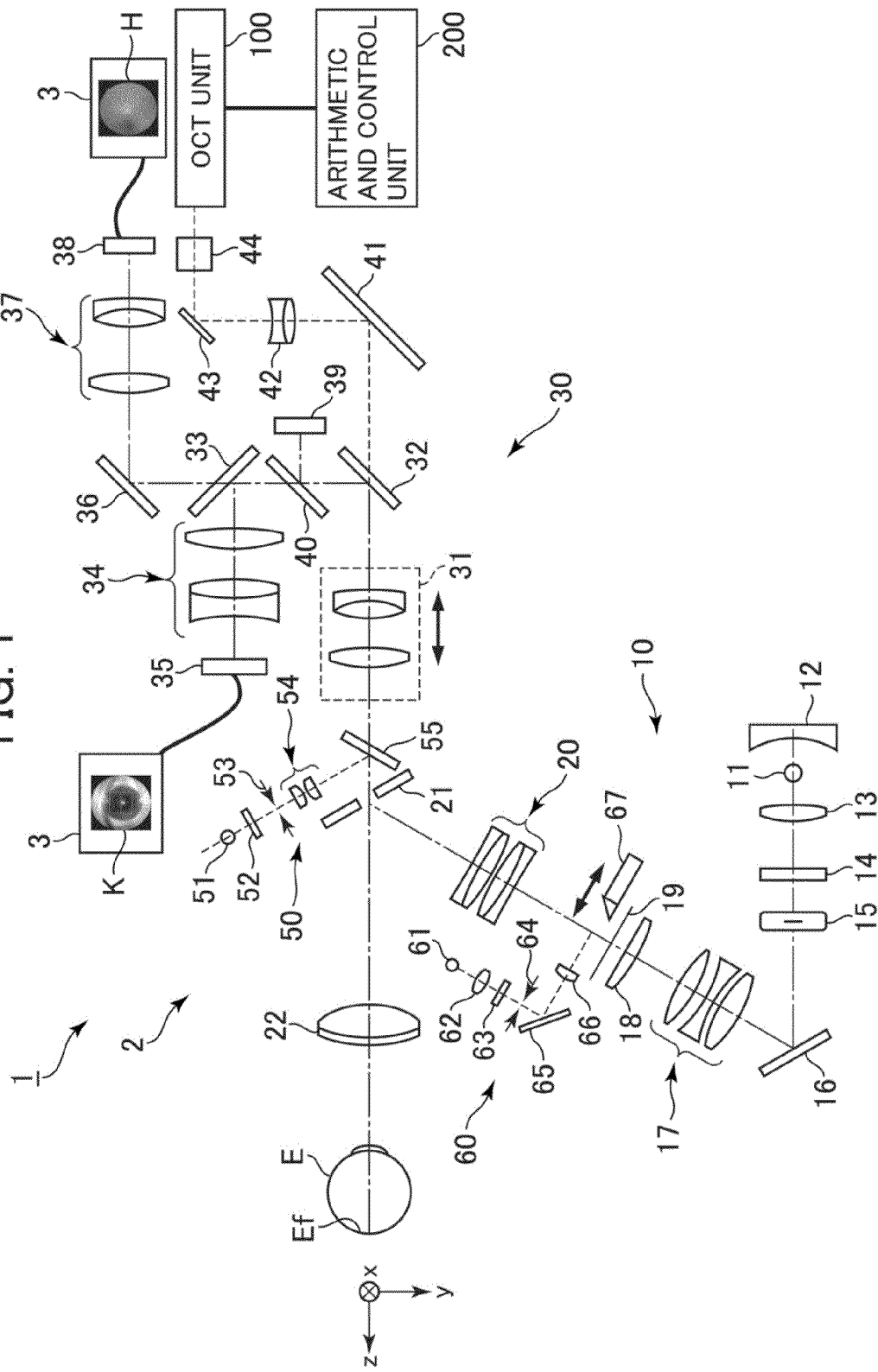
FIG. 1 is a schematic view showing an example of a configuration of an embodiment of a fundus observation apparatus according to the present invention.
Figure 2:
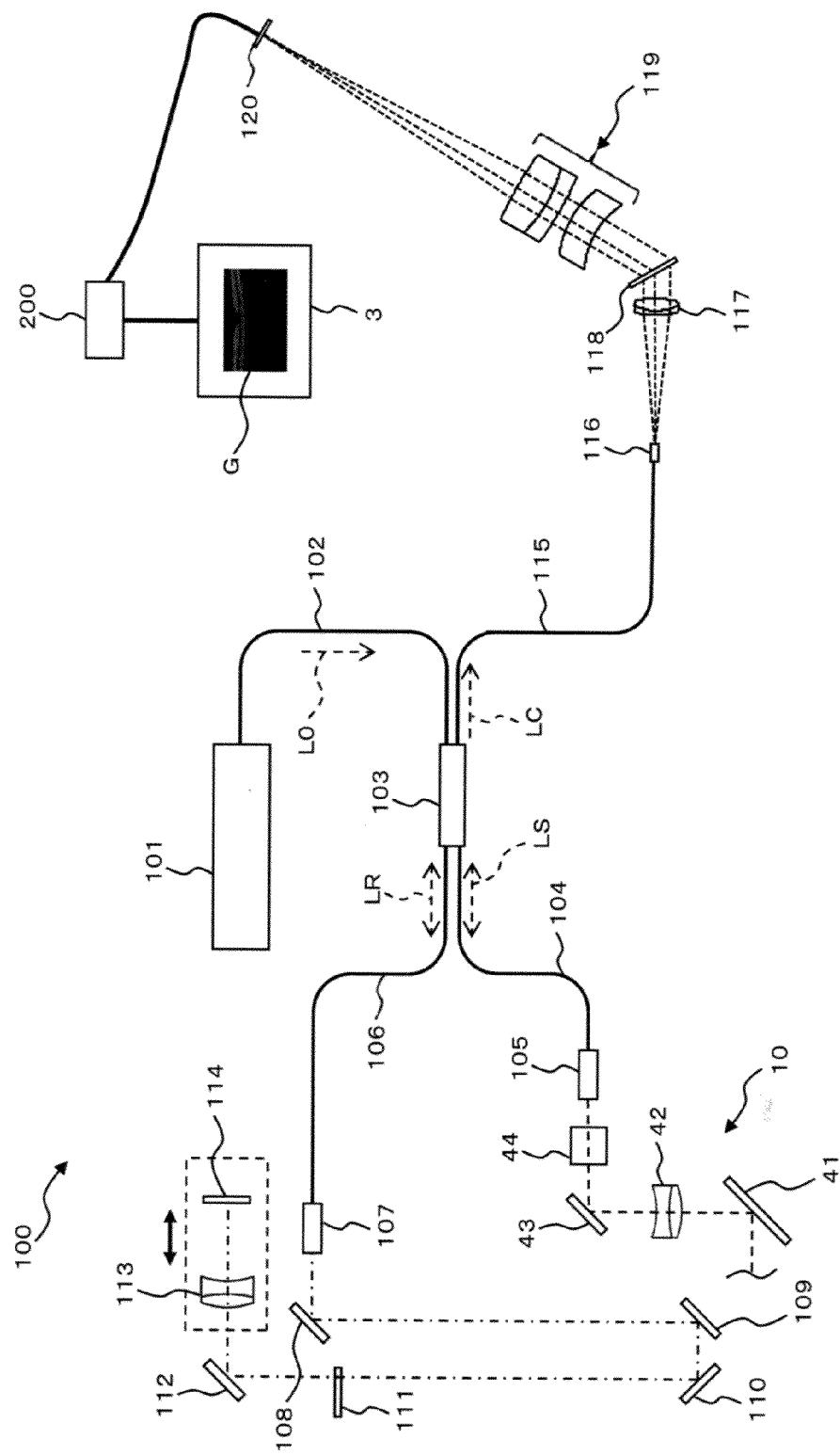
FIG. 2 is a schematic view showing an example of a configuration of an embodiment of a fundus observation apparatus according to the present invention.

A fundus observation apparatus 1, as shown in FIG. 1 and FIG. 2, includes a retinal camera unit 2, an OCT unit 100, and an arithmetic and control unit 200. The retinal camera unit 2 has almost the same optical system as a conventional retinal camera. The OCT unit 100 is provided with an optical system for obtaining an OCT image of a fundus. The arithmetic and control unit 200 is provided with a computer that executes various arithmetic processes, control processes, and so on.

[Retinal Camera Unit]

The retinal camera unit shown in FIG. 1 is provided with an optical system for forming a 2-dimensional image (fundus image) representing the surface morphology of the fundus Ef of an eye E. Fundus images include observation images, photographed images, etc. The observation image is, for example, a monochrome moving image formed at a prescribed frame rate using near-infrared light. The photographed image is, for example, a color image captured by flashing visible light. It should be noted that the retinal camera unit 2 may also be configured so as to be capable of capturing other types of images such as a fluorescein angiography image or an indocyanine green fluorescent image.

The retinal camera unit 2 is provided with a chin rest and a forehead placement for retaining the face of the subject, similar to a conventional retinal camera. Moreover, like a conventional retinal camera, the retinal camera unit 2 is provided with an illumination optical system 10 and an imaging optical system 30. The illumination optical system 10 radiates an illumination light to the fundus Ef. The imaging optical system 30 guides a fundus reflected light of the illumination light to imaging devices (CCD image sensors 35, 38). Moreover, the imaging optical system 30 guides a signal light LS coming from the OCT unit 100 to the fundus Ef, and guides the signal light propagated through the fundus Ef to the OCT unit 100.

An observation light source 11 of the illumination optical system 10 comprises, for example, a halogen lamp. Light (observation illumination light) output from the observation light source 11 is reflected by a reflection mirror 12 with a curved reflection surface, and becomes near infrared after passing through a visible cut filter 14 via a condenser lens 13. Furthermore, the observation illumination light is once converged near an imaging light source 15, reflected by a mirror 16, and passes through relay lenses 17, 18, diaphragm 19, and relay lens 20. Then, the observation illumination light is reflected on the peripheral part (the surrounding region of an aperture part) of an aperture mirror 21 and illuminates the fundus Ef via an object lens 22.

The fundus reflection light of the observation illumination light is refracted by the object lens 22, passes through the aperture part formed in the center region of the aperture mirror 21, passes through a dichroic mirror 55 and, travels through a focus lens 31, and is reflected by a dichroic mirror 32. Furthermore, the fundus reflection light passes through a half-mirror 40 and forms an image on the light receiving surface of the CCD image sensor 35 by a condenser lens 34 after being reflected by a dichroic mirror 33. The CCD image sensor 35 detects, for example, the fundus reflection light at a prescribed frame rate. An image (observation image) K based on the fundus reflection light detected by the CCD image sensor 35 is displayed on a display device 3.

The imaging light source 15 consists of, for example, a xenon lamp. The light (imaging illumination light) output from the imaging light source 15 is irradiated to the fundus Ef via a route that is the same as the observation illumination light. The fundus reflection light of the imaging illumination light is guided to the dichroic mirror 33 via the same route as that of the observation illumination light, passes through the dichroic mirror 33, and forms an image on the light receiving surface of the CCD image sensor 38 by a condenser lens 37 after being reflected by a mirror 36. An image (photographed image) H based on the fundus reflection light detected by the CCD image sensor 38 is displayed on the display device 3. It should be noted that the display device 3 for displaying an observation image K and the display device 3 for displaying a photographed image H may be the same or different.

An LCD (Liquid Crystal Display) 39 displays a fixation target or a visual target for measuring eyesight. The fixation target is a visual target for fixing the eye E, and is used when imaging a fundus or forming a tomographic image. The visual target for measuring eyesight is a visual target used for measuring an eyesight value of the eye E, for example, such as Landolt rings. It should be noted that the visual target for measuring eyesight is sometimes simply referred to as a target.

Part of the light output from the LCD 39 is reflected by a half-mirror 40, reflected by the dichroic mirror 32, passes through the aperture part of the aperture mirror 21 via the focus lens 31 as well as a dichroic mirror 55, is refracted by the object lens 22 and projected to the fundus Ef.

By changing a display position of the fixation target on the screen of the LCD 140, it is possible to change a fixation position of the eye E. As the fixation position of the eye E, there are a position for acquiring an image centered on the macula of the fundus Ef, a position for acquiring an image centered on the optic papilla, a position for acquiring an image centered on the fundus center between the macula and the optic papilla, and so on, as in conventional retinal cameras.

Furthermore, as with conventional fundus cameras, the retinal camera unit 2 is provided with an alignment optical system 50 and a focus optical system 60. The alignment optical system 50 generates a target (alignment target) for matching the position (alignment) of the device optical system with respect to the eye E. The focus optical system 60 generates a target (split target) for matching the focus with respect to the eye Ef.

Light (alignment light) output from the LED (Light Emitting Diode) 51 of the alignment optical system 50 is reflected by the dichroic mirror 55 via diaphragms 52, 53, and a relay lens 54, passes through the aperture part of the aperture mirror 21, and is projected onto the cornea of the eye E by the object lens 22.

Part of cornea reflection light of the alignment light is transmitted through the dichroic mirror 55 via the object lens 22 and the aperture part, passes through the focus lens 31, is reflected by the dichroic mirror 32, transmitted through the half-mirror 40, reflected by the dichroic mirror 33, and projected onto the light receiving surface of the CCD image sensor 35 by the condenser lens 34. A light receiving image (alignment target) by the CCD image sensor 35 is displayed on the display device 3 along with the observation image K. A user conducts alignment by an operation that is the same as conventional fundus cameras. It should be noted that alignment may be performed, by an arithmetic and control unit 200, as a result of analyzing the position of the alignment target and moving the optical system.

In order to conduct focus adjustment, the reflection surface of a reflection rod 67 is provided in a slanted position on the light path of the illumination optical system 10. Light (focus light) output from an LED 61 of the focus optical system 60 passes through a relay lens 62, is split into two light fluxes by a split target plate 63, passes through a two-hole diaphragm 64, is reflected by a mirror 65, and is reflected after an image is formed once on the reflection surface of the reflection rod 67 by a condenser lens 66. Furthermore, the focus light is reflected at the aperture mirror 21 via the relay lens 20 and an image is formed on the fundus Ef by the object lens 22.

The fundus reflection light of the focus light passes through the same route as the cornea reflection light of the alignment light and is detected by the CCD image sensor 35. A light receiving image (split target) by the CCD image sensor 35 is displayed on the display device 3 along with an observation image K. The arithmetic and control unit 200, as in the past, analyzes the position of the split target, and moves the focus lens 31 and the focus optical system 60 for focusing. It should be noted that focusing may be performed manually while visually recognizing the split target.

An optical path including a mirror 41, collimator lens 42, and Galvano mirrors 43, 44 is provided behind the dichroic mirror 32. The optical path is connected to the OCT unit 100.

The Galvano mirror 44 performs scanning with a signal light LS from the OCT unit 100 in the x-direction. The Galvano mirror 43 performs scanning with a signal light LS in the y-direction. Scanning may be performed with the signal light LS in an arbitrary direction in the xy-plane due to the two Galvano mirrors 43 and 44.

[OCT Unit]

The OCT unit 100 shown in FIG. 2 is provided with an optical system for obtaining a tomographic image of the fundus Ef. The optical system has a similar configuration to a conventional Fourier-Domain-type OCT device. That is to say, the optical system is configured to split a low coherence light into a reference light and a signal light, make the signal light propagated through a fundus and the reference light propagated through a reference optical path interfere with each other to generate an interference light, and detects the spectral components of this interference light. This detection result (detection signal) is transmitted to the arithmetic and control unit 200.

A light source unit 101 outputs a low coherence light L0. The low coherence light L0 is, for example, light (invisible light) consisting of wavelengths that is impossible to be detected by human eyes. Furthermore, the low coherence light L0 is, for example, near-infrared light having the center wave of about 1050-1060 nm. The light source unit 101 is configured to include light output device, such as an SLD (super luminescent diode), SOA (Semiconductor Optical Amplifier) and the like.

The low coherence light L0 output from the light source unit 101 is guided to a fiber coupler 103 by an optical fiber 102 and split into signal light LS and reference light LR. It should be noted that the fiber coupler 103 acts both as a means to split light (splitter) as well as a means to synthesize light (coupler), but herein the same is conventionally referred to as a "fiber coupler."

The signal light LS is guided by the optical fiber 104 and becomes a parallel light flux by a collimator lens unit 105. Furthermore, the signal light LS is reflected by Galvano mirrors 44 and 43, converged by the collimator lens 42, reflected by the mirror 41, transmitted through a dichroic mirror 32, and irradiated to the fundus Ef after passing through a route that is the same as the light from the LCD 39. The signal light LS is scattered and reflected at the fundus Ef. The scattered light and the reflection light are sometimes all together referred to as the fundus reflection light of the signal light LS. The fundus reflection light of the signal light LS progresses along the same route in the reverse direction and is guided to the fiber coupler 103.

The reference light LR is guided by an optical fiber 106 and becomes a parallel light flux by a collimator lens unit 107. Furthermore, the reference light LR is reflected by mirrors 108, 109, 110, dimmed by an ND (Neutral Density) filter 111, and reflected by a mirror 112, with the image formed on a reflection surface of a reference mirror 114 by a collimator lens 113. The reference light LR reflected by the reference mirror 114 progresses along the same route in the reverse direction and is guided to the fiber coupler 103. It should be noted that an optical element (pair prism, etc.) for dispersion compensation and/or an optical element for polarization correction (wave plate, etc.) may also be provided for the optical path (reference optical path) of the reference light LR.

The fiber coupler 103 superposes the fundus reflection light of the signal light LS and the reference light LR reflected by the reference mirror 114. Interference light LC thus generated is guided by an optical fiber 115 and output from an incidental end 116. Furthermore, the interference light LC is converted to a parallel light flux by a collimator lens 117, spectrally divided (spectrally decomposed) by a diffraction grating 118, converged by the convergence lens 57, and projected onto the light receiving surface of a CCD image sensor 120.

The CCD image sensor 120 is for example a line sensor, and detects the respective spectral components of the divided interference light LC and converts the components into electric charges. The CCD image sensor 120 accumulates these electric charges and generates a detection signal. Furthermore, the CCD image sensor 120 transmits the detection signal to the arithmetic and control unit 200.

Although a Michelson-type interferometer is employed in this embodiment, it is possible to employ any type of interferometer such as a Mach-Zehnder-type as necessary. Instead of a CCD image sensor, other types of image sensors, such as a CMOS (Complementary Metal Oxide Semiconductor) image sensor, can be used.

[Arithmetic and Control Unit]

A configuration of the arithmetic and control unit 200 will be described. The arithmetic and control unit 200 analyzes the detection signals inputted from the CCD image sensor 120, and forms an OCT image of the fundus Ef. An arithmetic process for this is like that of a conventional Fourier-Domain-type OCT device.

Further, the arithmetic and control unit 200 controls each part of the retinal camera unit 2, the display device 3 and the OCT unit 100.

As control of the retinal camera unit 2, the arithmetic and control unit 200 executes: control of action of the observation light source 101, the imaging light source 103 and LED's 51 and 61; control of action of the LCD 39; control of movement of the focus lens 31; control of movement of the reflection rod 67; control of movement of the focus optical system 60; control of action of the respective Galvano mirrors 43 and 44; and so on.

Further, as control of the OCT unit 100, the arithmetic and control unit 200 executes: control of action of the light source unit 101; control of movement of the reference mirror 114 and the collimator lens 113; control of action of the CCD image sensor 120; and so on.

The arithmetic and control unit 200 includes a microprocessor, a RAM, a ROM, a hard disk drive, a communication interface, and so on, as in conventional computers. The storage device such as the hard disk drive stores a computer program for controlling the fundus observation apparatus 1. The arithmetic and control unit 200 may be provided with a circuit board dedicated for forming OCT images based on detection signals from the CCD image sensor 120. Moreover, the arithmetic and control unit 200 may be provided with operation devices (imput devices) such as a keyboard and a mouse, and/or display devices such as LCD.

The retinal camera unit 2, display device 3, OCT unit 100, and arithmetic and control unit 200 may be integrally configured (that is, within a single case), or configured as individual separate bodies.

[Control System]

Figure 3:
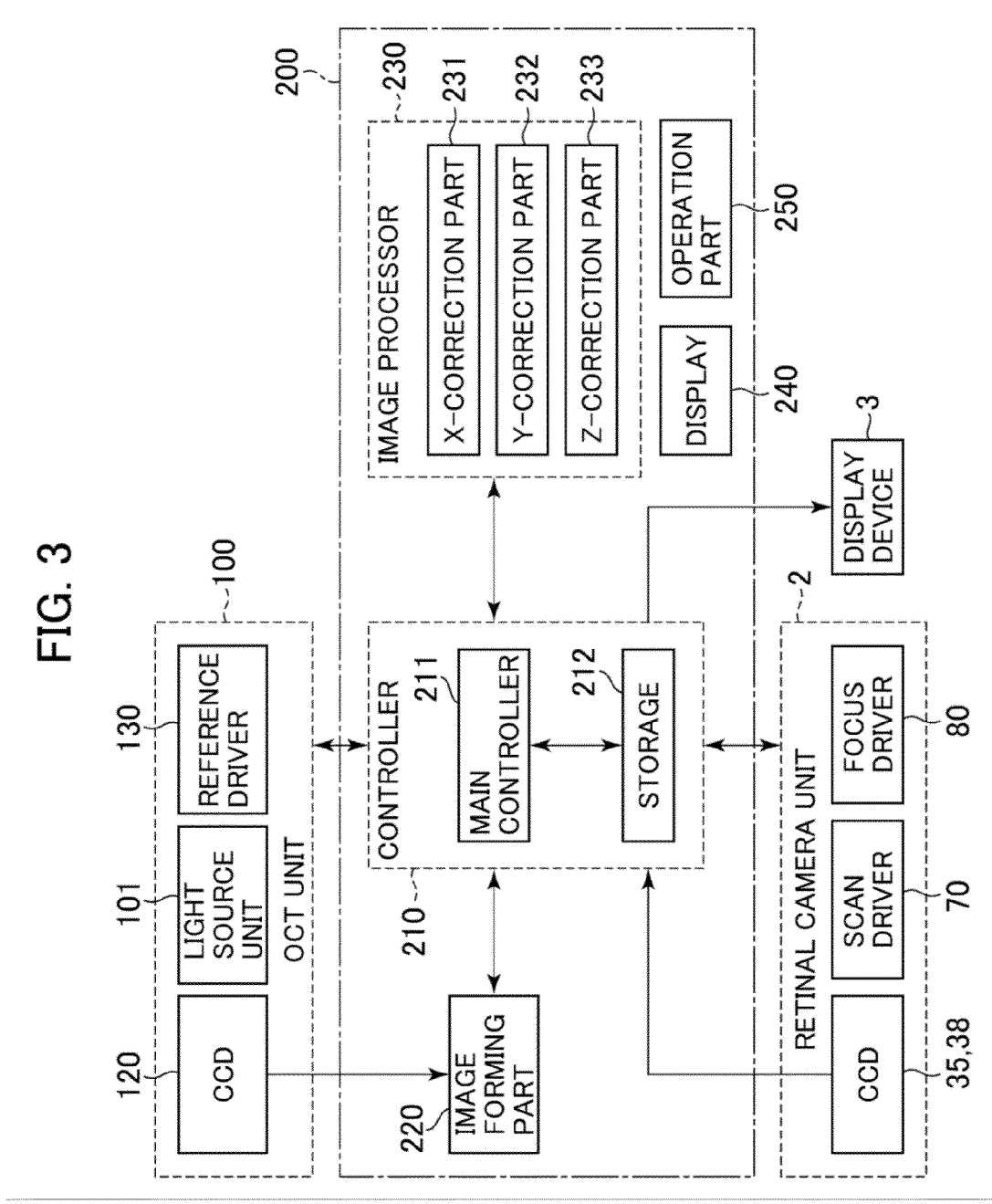
FIG. 3 is a schematic block diagram showing an example of a configuration of an embodiment of a fundus observation apparatus according to the present invention.

A configuration of a control system of the fundus observation apparatus 1 will be described with reference to FIG. 3.

(Controller)

The control system of the fundus observation apparatus 1 has a configuration centered on a controller 210 of the arithmetic and control unit 200. The controller 210 includes, for example, the aforementioned microprocessor, RAM, ROM, hard disk drive, and communication interface.

A controller 210 is provided with a main controller 211 and storage 212. The main controller 211 performs the aforementioned various kinds of control. Specifically, the main controller 211 controls a scan driver 70 as well as a focus driver 80 of the retinal camera unit 2, and further controls a reference driver 130 of the OCT unit 100.

The scan driver 70 is configured, for example, including a servo motor and independently changes the facing direction of the Galvano mirrors 43 and 44. The scan driver 70 consists of one example of the "scanning part" in the present invention along with the Galvano mirrors 43 and 44.

The focus driver 80 is configured, for example, including a pulse motor and moves the focus lens 31 in the optical axis direction. Thereby, the focus position of light towards the fundus Ef is changed.

The reference driver 130 is configured, for example, including a pulse motor and integrally moves the collimator lens 113 as well as the reference mirror 114 along the travelling direction of the reference light LR.

The main controller 211 executes a process of writing data into the storage 212, and a process of reading out the data from the storage 212.

The storage 212 stores various kinds of data. The data stored in the storage 212 is, for example, image data of OCT images, image data of fundus images, and eye information. The eye information includes information on the eye, for example, information on a subject such as a patient ID and a name, information on identification of left eye or right eye, and so on.

(Image Forming Part)

An image forming part 220 forms image data of a tomographic image of the fundus Ef based on the detection signals from the CCD image sensor 120. Like the conventional Fourier-Domain OCT, this process includes processes such as noise elimination (noise reduction), filtering, and FFT (Fast Fourier Transform).

The image forming part 220 includes, for example, the aforementioned circuit board and communication interface. It should be noted that "image data" and the "image" presented based on the image data may be identified with each other in this specification.

(Image Processor)

An image processor 230 executes various image processing and analysis on images formed by the image forming part 220. For example, the image processor 230 executes various correction processes such as luminance correction and dispersion correction of images.

Further, the image processor 230 executes, for example, an interpolation process of interpolating pixels between tomographic images formed by the image forming part 220, thereby forming image data of a three-dimensional image of the fundus Ef.

Image data of a three-dimensional image refers to image data that the positions of pixels are defined by the three-dimensional coordinates. The image data of a three-dimensional image is, for example, image data composed of three-dimensionally arranged voxels. This image data is referred to as volume data, voxel data, or the like. For displaying an image based on the volume data, the image processor 230 executes a rendering process (such as volume rendering and MIP (Maximum Intensity Projection)) on this volume data, and forms image data of a pseudo three-dimensional image taken from a specific view direction. On a display device such as the display 240, this pseudo three-dimensional image is displayed.

Further, it is also possible to form stack data of a plurality of tomographic images as the image data of a three-dimensional image. Stack data is image data obtained by three-dimensionally arranging a plurality of tomographic images obtained along a plurality of scanning lines, based on the positional relation of the scanning lines. That is to say, stack data is image data obtained by expressing a plurality of tomographic images defined by originally individual two-dimensional coordinate systems by a three-dimensional coordinate system (namely, embedding into a three-dimensional space).

The image processor 230 includes, for example, the aforementioned microprocessor, RAM, ROM, hard disk drive, circuit board, and so on.

The image processor 230 has an x-correction part 231, y-correction part 232, and z-correction part 233. The x-correction part 231, y-correction part 232, and z-correction part 233 respectively perform positional corrections of a 3-dimensional image in the x-direction (horizontally), y-direction (vertically), and z-direction (depthwise). The x-direction and the y-direction are directions along the surface of the fundus Ef (fundus surface direction). Furthermore, the z-direction is a direction depthwise of the fundus Ef (fundus depth direction). These correction parts 231 to 233 are one example of the "correction part" in the present invention. Hereinafter, processes executed by these correction parts 231 to 233 are explained.

The x-correction part 231 corrects the position in the x-direction of a plurality of tomographic images captured by three-dimensional scanning described below, thereby corrects the position in the x-direction of a 3-dimensional image based on these tomographic images. In three-dimensional scanning, scanning is performed with the signal light LS along a plurality of scanning lines arranged in the y-direction. Each scanning line includes a plurality of linearly arranged scanning points in the x-direction. When performing three-dimensional scanning, the observation image K (moving image) of the fundus Ef is simultaneously captured. When capturing the observation image K, the frame rate is set so as to capture still images (frames) corresponding to scanning along each scanning line. Consequently, it becomes possible to associate a still image with each scanning line (each tomographic image).

Because three-dimensional scanning takes approximately a few seconds, there is a risk of the eye E moving (fixation misalignment, etc.) or blinking during scanning.

Figure 4:
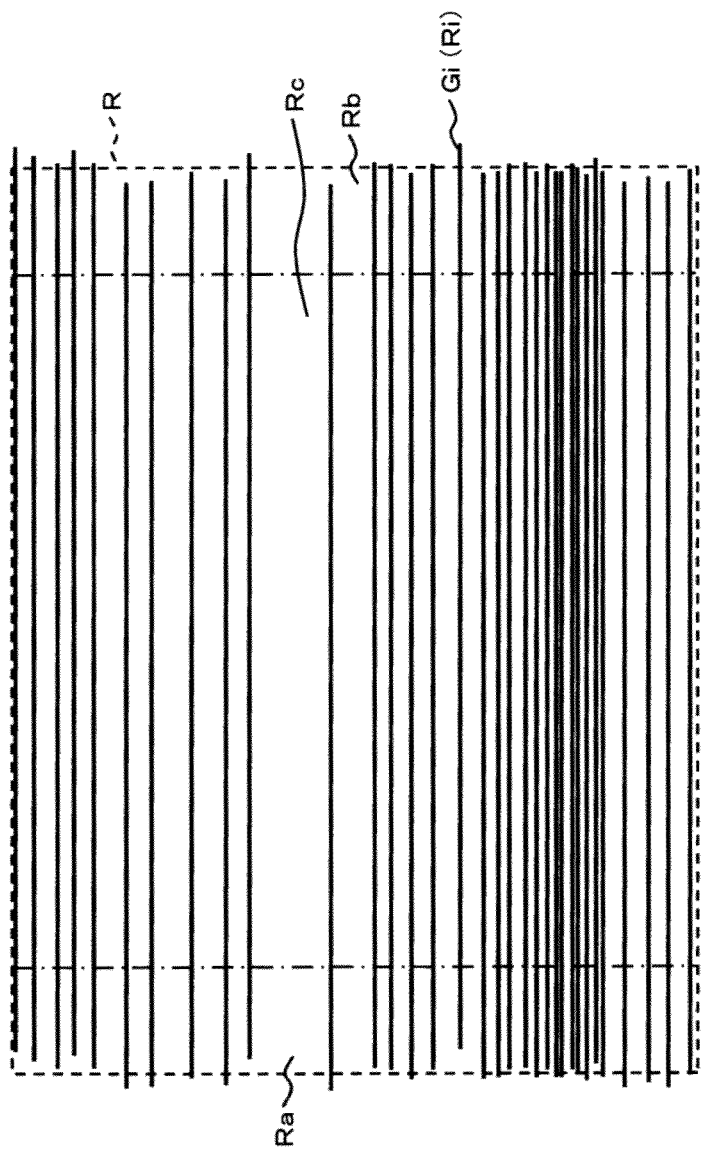
FIG. 4 is a schematic view for explaining an example of an action of an embodiment of a fundus observation apparatus according to the present invention.

FIG. 4 shows an example of an arranged state of a plurality of tomographic images Gi (i=m) obtained when such a problem occurs during an OCT measurement. FIG. 4 represents the arrangement of tomographic images Gi when the fundus Ef is seen from the side of the fundus observation apparatus 1. It should be noted that, in a state in which the problem is not generated, tomographic images Gi are arranged at equal intervals within a scanning region R, without misalignment in the x-direction (the direction along each scanning line Ri).

As described previously, when performing three-dimensional scanning, the observation image K of the fundus Ef is simultaneously captured and still images (frames) corresponding to each scanning line Ri (each tomographic image Gi) are obtained. The x-correction part 231 analyzes the pixel values (luminance values) of each still image and specifies an image region of a characteristic site of the fundus Ef in the still image. For example, optic papilla, macula, blood vessels, branching parts of blood vessels, lesions, etc. are cited as characteristic sites.

Next, the x-correction part 231 calculates the positional misalignment amount of the above image region in these still images. This process is, for example, to calculate the displacement of the above image region in still images corresponding to each of the other tomographic images G2 to Gm with respect to the above image region in a still image corresponding to the first fundus image G1 (standard still image). The displacement calculated herein is the displacement in the x-direction and the displacement in the y-direction.

Subsequently, the x-correction part 231 corrects the relative position in the x-direction of the plurality of tomographic images Gi so as to cancel the calculated positional misalignment amount (displacement). Thereby, the position in the x-direction of a 3-dimensional image based on the plurality of tomographic images Gi is corrected.

Furthermore, the x-correction part 231 deletes a part (end part region) of each tomographic image Gi that is included in the end part regions Ra and Rb of a scanning region R. Consequently, it becomes possible to obtain a 3-dimensional image of the center portion (image region) Rc of the scanning region R.

As in the x-correction part 231, the y-correction part 232 corrects the relative position in the y-direction of the plurality of tomographic images Gi so as to cancel the above positional misalignment amount (displacement) calculated based on still images. Thereby, the position of a 3-dimensional image in the y-direction based on the plurality of tomographic images Gi is corrected. It should be noted that the calculation process of the positional misalignment amount may be conducted by the y-correction part 232.

Furthermore, the y-correction part 232 adjusts the intervals of the plurality of tomographic images Gi after the relative position is corrected as described above. For this process, there is a process (supplementary process) of filling in (supplementing) portions where tomographic images are sparse, and a process of thinning portions where tomographic images are dense (thinning process).

The supplementary process is performed, for example, as below. First, the y-correction part 232 calculates the interval of adjacent tomographic images Gi, G(i+1) (i=1 to m−1). In this process, it is also possible to count the number of tomographic images Gi included in a partial region of a prescribed size within the scanning region R to obtain the density of the tomographic images Gi.

Next, the y-correction part 232 determines whether the calculated interval is equal to or greater than a prescribed value or not. The prescribed value is set, for example, based on the size of the scanning region R and the number of scanning lines Ri. It should be noted that obtaining the density of the tomographic images Gi ends up determining whether the density is equal to or less than a prescribed value or not.

When determined that the interval is equal to or greater than the prescribed value, the controller 210 controls the scan driver 70 and rescans with a signal light LS along the scanning lines located within a region sandwiched by two tomographic images with an interval that is equal to or greater than the prescribed value.

The image forming part 220 forms a new tomographic image based on the detection results of interference light of the rescanned signal light LS and reference light LR, and the image processor 230 forms a 3-dimensional image corresponding to the above region based on these new tomographic images.

Moreover, the y-correction part 232 may perform the following process. First, the y-correction part 232 determines whether each positional misalignment amount calculated based on a plurality of still images is equal to or greater than a prescribed value or not.

When determined that the positional misalignment amount is equal to or greater than the prescribed value, the controller 210 controls the scan driver 70 and rescans with the signal light LS along a scanning line located at a region close to the scanning line of a tomographic image corresponding to a still image whose positional misalignment amount is determined to be equal to or greater than the prescribed value.

The image forming part 220 forms a new tomographic image along the rescanned scanning line, based on the detection results of interference light of the rescanned signal light LS and reference light LR.

Furthermore, the y-correction part 232 may also perform the following process. First, for each of a plurality of scanning lines, the y-correction part 232 selects a tomographic image closest to the original position of the scanning line among the plurality of tomographic images Gi, based on the calculated positional misalignment amount based on the plurality of still images. The original position of a scanning line is represented by a coordinate value of a scanning line set within the scanning region R. This coordinate value (particularly a y-coordinate value) is easily obtained based on the size of the scanning region R and the number of scanning lines. The y-correction part 232 selects the tomographic image located closest to this coordinate position.

The image processor 230 forms a 3-dimensional image based only on the selected tomographic images.

Furthermore, the y-correction part 232 may also perform a process such as follows. After the relative position of the plurality of tomographic images Gi is corrected, the y-correction part 232 calculates the interval of these tomographic images Gi. The image processor 230 forms, based on the calculated intervals as well as these tomographic images Gi, a plurality of tomographic images arranged at equal intervals. In this process, the pixel value at positions arranged at equal intervals in the y-direction is calculated, for example, by performing a linear interpolation process based on the pixel values (luminance values) at scanning points arranged in the y-direction. A plurality of tomographic images arranged at equal intervals is obtained by forming images using a calculated pixel value. Furthermore, the image processor 230 forms a 3-dimensional image based on these tomographic images arranged at equal intervals.

There is a risk in that the image region of a characteristic site is not specified from the observation image K (a plurality of still images). If so, the correction process described above cannot be performed. In such a case, the process as below may be performed.

If there exists a still image for which an image region of a characteristic site is not specified, the y-correction part 232 specifies a scanning line of a tomographic image corresponding to the still image. The still images and the tomographic images are associated as described previously, and so the tomographic images and the scanning lines are associated as a one-to-one correspondence; hence, making it possible to carry out this process easily.

Subsequently, the controller 210 controls the scan driver 70 and rescans with a signal light LS along the specified scanning line. Then, the observation image K is also captured.

The image forming part 220 forms a new tomographic image along the specified scanning line, based on the detection results of interference light of the rescanned signal light LS and reference light LR. The x-correction part 231 and the y-correction part 232 are capable of performing the above correction process, based on the new tomographic image and the new observation image K. Furthermore, the image processor 230 is capable of forming a 3-dimensional image of a region corresponding to the specified scanning line, based on the new tomographic image.

As described previously, the z-correction part 233 corrects a position in the z-direction of a 3-dimensional image (plurality of tomographic images Gi). For this purpose, scanning (separate scanning) is performed separately from three-dimensional scanning. The separate scanning consists of scanning in the direction crossing the plurality of scanning lines Ri. In the present embodiment, as separate scanning, scanning with the signal light LS is performed along each of a prescribed number of scanning lines (scanning lines for correction) orthogonal to the plurality of scanning lines Ri.

The image forming part 220 forms a tomographic image (tomographic image for correction) corresponding to each scanning line for correction, based on the detection results of interference light LC obtained by the separate scanning.

The z-correction part 233 specifies an image region of a characteristic layer of the fundus Ef in a prescribed number of formed tomographic images for correction. As for the characteristic layer, it is desirable to select a site that can be easily specified in a tomographic image, for example, a site (organ) clearly depicted with high luminance.

Subsequently, the z-correction part 233 moves each tomographic image Gi in the fundus depth direction (z-direction) so as to match the depthwise position (z-coordinate value) of the image region in a tomographic image for correction and the depthwise position of the image region of the characteristic layer in each tomographic image Gi. Thereby, the positional correction in the fundus depth direction of a 3-dimensional image becomes possible.

The image forming part 220 and the image processor 230 are an example of the "image forming part" of the present invention.

(Display and Operation Part)

The display 240 is configured including a display device of the aforementioned arithmetic and control unit 200. The operation part 250 is configured including an operation device of the aforementioned arithmetic and control unit 200. Furthermore, the operation part 250 may also include various kinds of buttons or keys provided with the case of the fundus observation apparatus 1 or its outside. For example, if the retinal camera unit 2 has a case that is the same as conventional fundus cameras, a joy stick, operation panel, etc. provided with the case may also be included in the operation part 250. Furthermore, the display 240 may also include various display devices such as a touch panel monitor, etc. provided with the case of the retinal camera unit 2.

The display 240 and the operation part 250 do not need to be composed as separate devices. For example, like a touch panel LCD, a device in which the display function and the operation function are integrated can be used.

[Scan with Signal Light and OCT Image]

A scan with the signal light LS and an OCT image will be described.

The scan aspect of the signal light LS by the fundus observation apparatus 1 is, for example, a horizontal scan, vertical scan, cruciform scan, radial scan, circular scan, concentric scan, and helical scan. These scan aspects are selectively used as necessary in consideration of an observation site of the fundus, an analysis target (the retinal thickness or the like), a time required to scan, the accuracy of a scan, and so on.

A horizontal scan is a scan with the signal light LS in the horizontal direction (x-direction). The horizontal scan includes an aspect of scanning with the signal light LS along a plurality of scanning lines extending in the horizontal direction arranged in the vertical direction (y-direction). In this aspect, it is possible to set any interval between scanning lines. By setting the interval between adjacent scanning lines to be sufficiently narrow, it is possible to form the aforementioned three-dimensional image (three-dimensional scan). A vertical scan is also performed in a similar manner.

A cruciform scan is a scan with the signal light LS along a cross-shape trajectory formed by two linear trajectories (line trajectories) orthogonal to each other. A radial scan is a scan with the signal light LS along a radial trajectory formed by a plurality of line trajectories arranged at predetermined angles. The cruciform scan is an example of the radial scan.

A circular scan is a scan with the signal light LS along a circular trajectory. A concentric scan is a scan with the signal light LS along a plurality of circular trajectories arranged concentrically around a predetermined center position. The circular scan is regarded as a special example of the concentric scan. A helical scan is a scan with the signal light LS along a helical trajectory while making the turning radius gradually smaller (or greater).

With the configuration as described before, the Galvano mirrors 43 and 44 are capable of scanning with the signal light LS in the x-direction and the y-direction independently, and is therefore capable of scanning with the signal light LS along an arbitrary trajectory on the xy-plane. Thus, it is possible to realize various types of scan aspects as described above.

By scanning the signal light LS in the mode described above, it is possible to form tomographic images of the depth-wise direction (z-direction) along scanning lines (scan trajectory). Moreover, in a case that the interval between scanning lines is narrow, it is possible to form the aforementioned three-dimensional image.

A region on the fundus Ef subjected to scanning by the signal light LS as above is referred to as a scanning region as previously described. For example, a scanning region in three-dimensional scanning is a rectangular-shaped region in which a plurality of horizontal scans are arranged (refer to the scanning region R of FIG. 4). Furthermore, a scanning region in a concentric circular scan is a disc-shaped region surrounded by the trajectories of a circular scan of a maximum diameter. Moreover, the scanning region in a radial scan is a disc-shaped (or polygonal-shaped) region linking end positions of scanning lines.

[Actions and Effects]

The actions and effects of the fundus observation apparatus 1 as described above will be described.

According to the fundus observation apparatus 1, even if tomographic images Gi such as the set shown in FIG. 4 is obtained, the position in the x-direction and the y-direction of the tomographic images Gi (3-dimensional image) may be corrected, based on the observation image K.

Figure 5:
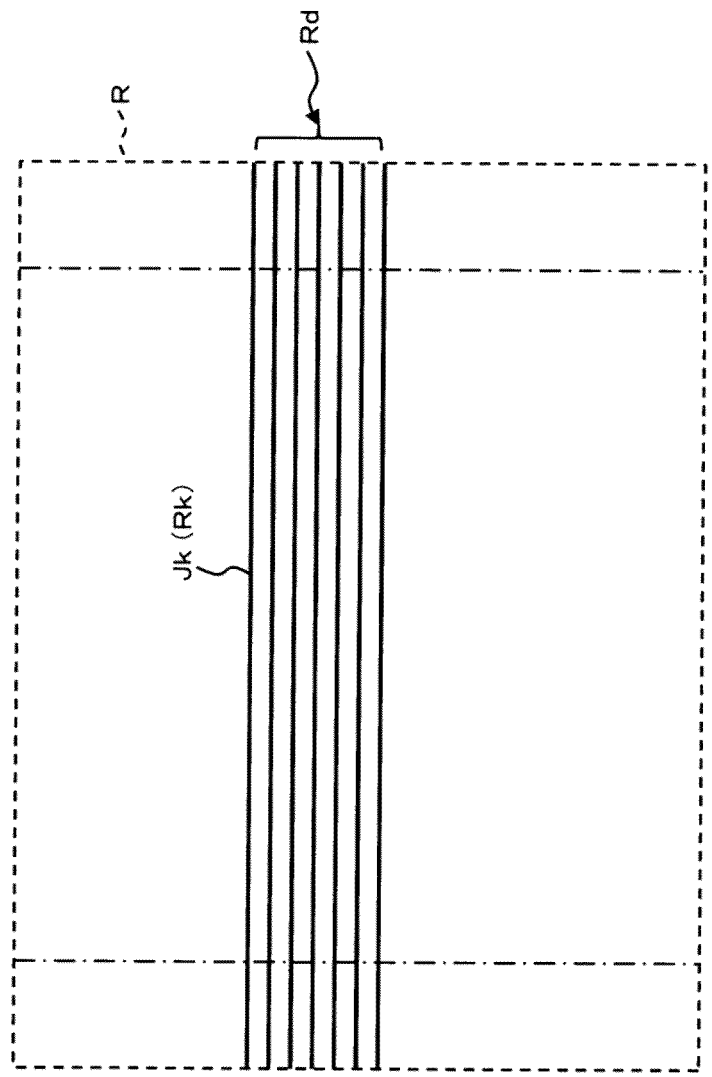
FIG. 5 is a schematic view for explaining an example of an action of an embodiment of a fundus observation apparatus according to the present invention.

Furthermore, according to the fundus observation apparatus 1, with regard to a region where the tomographic images Gi (scanning line Ri) are sparse, scanning may be performed again to complement a tomographic image. Thereby, as shown in FIG. 5, new tomographic images Jk are obtained along a scanning line Rk in a sparse region Rd and a 3-dimensional image in the sparse region Rd may be formed based on these new tomographic images Jk.

Furthermore, according to the fundus observation apparatus 1, tomographic images Gi may be thinned with regard to a portion where the tomographic images Gi are dense.

A plurality of tomographic images arranged at favorable intervals may be obtained and a favorable 3-dimensional image may be obtained via such a complement or thinning.

Figure 6A:
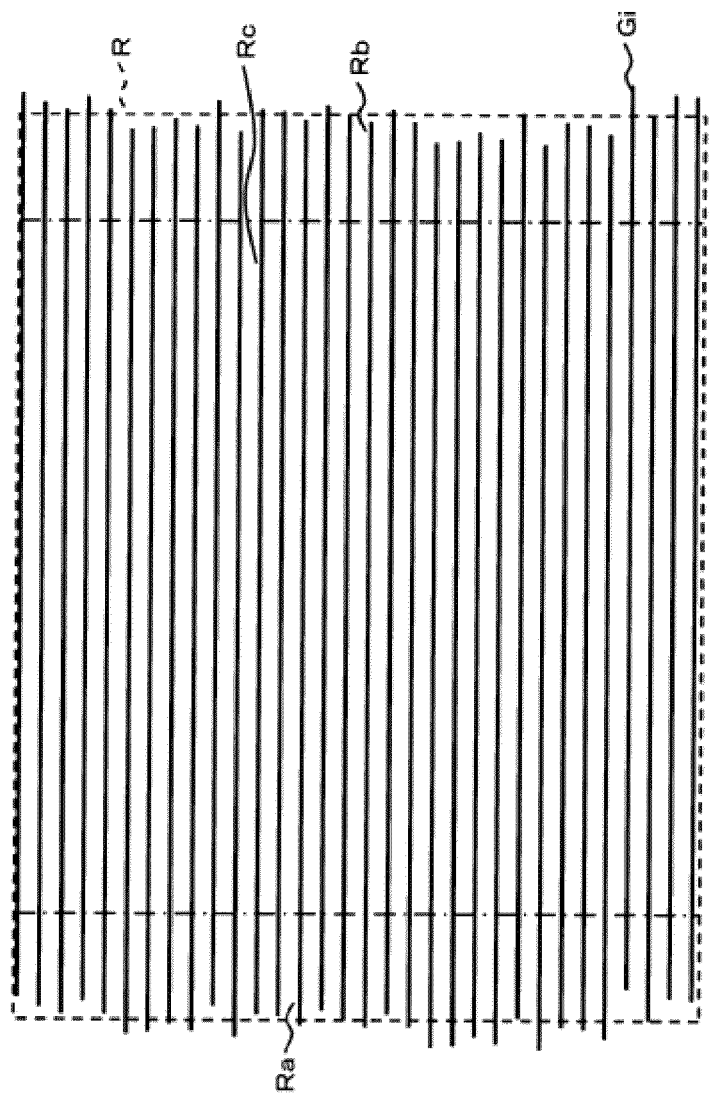
FIG. 6A is a schematic view for explaining an example of an action of an embodiment of a fundus observation apparatus according to the present invention.
Figure 6B:
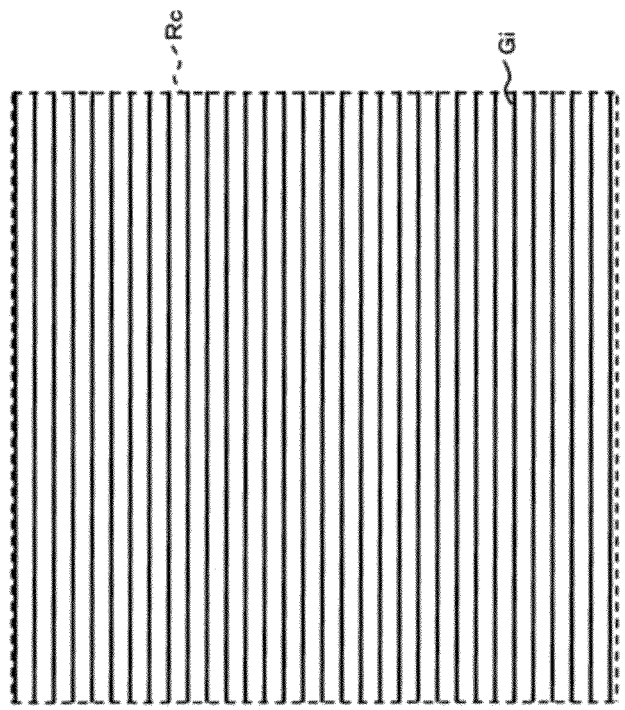
FIG. 6B is a schematic view for explaining an example of an action of an embodiment of a fundus observation apparatus according to the present invention.

Furthermore, according to the fundus observation apparatus 1, as shown in FIG. 6A and FIG. 6B, because a part (end part region) of each tomographic image Gi included in the end part regions Ra and Rb of a scanning region R may be deleted, a 3-dimensional image of the center portion (image region) Rc of the scanning region R is obtained.

Furthermore, according to the fundus observation apparatus 1, the position of a 3-dimensional image in the fundus depth direction may be corrected, based on tomographic images (tomographic images for correction) based on the detection results of interference light LC of signal light LS scanned separately from the three-dimensional scanning and reference light LR.

Furthermore, according to the fundus observation apparatus 1, intervals of a plurality of tomographic images Gi after the relative position is corrected, and a plurality of tomographic images arranged at equal intervals are formed, based on the calculated interval and the plurality of tomographic images Gi; thereby, making it possible to form a 3-dimensional image based on these tomographic images of equal intervals.

Furthermore, according to the fundus observation apparatus 1, an image region of a characteristic site of the fundus Ef in each still image consisting of the observation image K may be specified to calculate the positional misalignment amount of these image regions and, if determined that the positional misalignment amount is equal to or greater than a prescribed value, a new tomographic image may be formed by rescanning with the signal light LS along a scanning line located in a region close to the scanning line of a tomographic image corresponding to the still image whose positional misalignment amount is determined to be equal to or greater than the prescribed value; thereby, making it possible to form a 3-dimensional image corresponding to the above close region based on the new tomographic image.

Furthermore, according to the fundus observation apparatus 1, with regard to each scanning line Ri, based on the above calculated positional misalignment amount, the tomographic image closest to the original position of the scanning line Ri among the plurality of tomographic images Gi is selected; thereby, making it possible to form a 3-dimensional image based on the selected tomographic image.

Moreover, according to the fundus observation apparatus 1, when there exists a still image in which an image region of a characteristic site is not specified, a scanning line of a tomographic image corresponding to the still image is specified, and a new tomographic image is formed by rescanning with the signal light LS along the specified scanning line; thereby, making it possible to form a 3-dimensional image of a region corresponding to the scanning line based on the new tomographic image.

According to the fundus observation apparatus 1 that acts as described, even if the eye E moves or blinks during scanning with the signal light LS, a highly accurate 3-dimensional image may be obtained.

Second Embodiment

In the first embodiment, a technology for correcting the positional misalignment for each tomographic image is described. As described previously, each scanning line consists of a plurality of scanning points. The second embodiment describes a technology for obtaining the positional misalignment amount for one or more scanning point(s) as a unit. The obtained positional misalignment amount may be used for correcting positional misalignment as in the first embodiment in addition to being used for other purposes. As an example of other purposes, the second embodiment describes an application to a technology for forming a highly precise image by superposing more than two images obtained by scanning the same site of a fundus.

The fundus observation apparatus in the present embodiment carries out measurements that are the same as in the first embodiment and forms 1-dimensional images extending depthwise of a fundus at each scanning point. This 1-dimensional image is hereinafter referred to as an A-scan image. A tomographic image is formed by arranging a plurality of A-scan images according to the arrangement of a plurality of scanning points.

Furthermore, the fundus observation apparatus detects the position of a fundus at a prescribed time interval when scanning with signal light is executed, and calculates a positional misalignment amount of the plurality of A-scan images in the fundus surface direction (xy-direction) based on temporal changes in the detected position of the fundus.

Figure 7A:
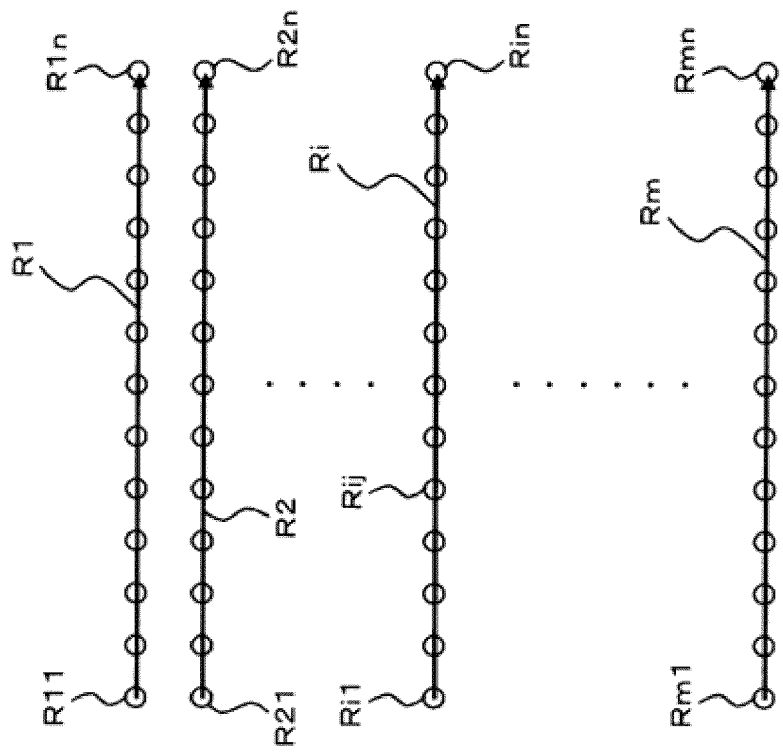
FIG. 7A is a schematic view for explaining positional misalignment of 1-dimensional images (A-scan images) extending depthwise of a fundus.
Figure 7B:
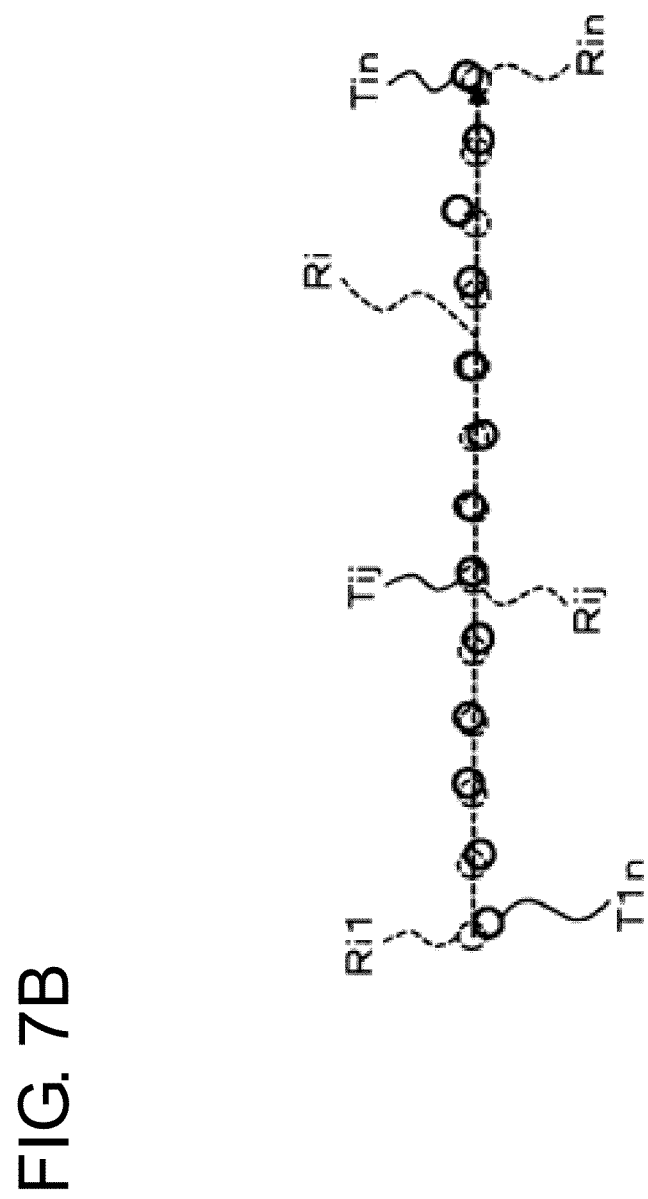
FIG. 7B is a schematic view for explaining positional misalignment of 1-dimensional images (A-scan images) extending depthwise of a fundus.

Herein, the positional misalignment of an A-scan image is described with reference to FIG. 7A and FIG. 7B. FIG. 7A shows an example of the arrangement of a plurality of scanning points Rij (i=1 to m, j=1 to n). Signal light LS is irradiated toward each scanning point Rij. However, if the eye E moves during measurement, as shown in FIG. 7B, the actual irradiation position Tij of the signal light LS ends up being shifted from the original position of the scanning point Rij.

As a result, the position of the A-scan image that should depicts the position of the fundus Ef corresponding to the scanning point Rij ends up being shifted (that is, ends up obtaining an A-scan image depicting the position of the fundus Ef corresponding to the actual irradiation position Tij). This is the positional misalignment of the A-scan image. In the present embodiment, the amount of positional misalignment (positional misalignment amount) of such an A-scan image is obtained.

At this time, the positional misalignment amount of each A-scan image may be obtained, or the positional misalignment amount of a continuous prescribed number of A-scan images may also be obtained all together. It should be noted that the first embodiment is one example of the latter process in which the positional misalignment amount of n number of A-scan images on each scanning line Ri are obtained all together.

The positional misalignment amount of the A-scan images is a vector quantity. That is, the positional misalignment amount includes information representing the displacement direction of the actual irradiation position Tij with respect to the scanning point Rij (misalignment direction information) and information representing the displacement amount (misalignment amount information).

[Configuration]

The fundus observation apparatus according to the present embodiment has the following configuration in order to realize a process as above. First, the fundus observation apparatus has a hardware configuration that is the same as that in the first embodiment. That is, the fundus observation apparatus is of the configuration shown in FIG. 1 and FIG. 2. Hereinafter, these figures are appropriately used as a reference for the explanation.

[Control System]

Figure 8:
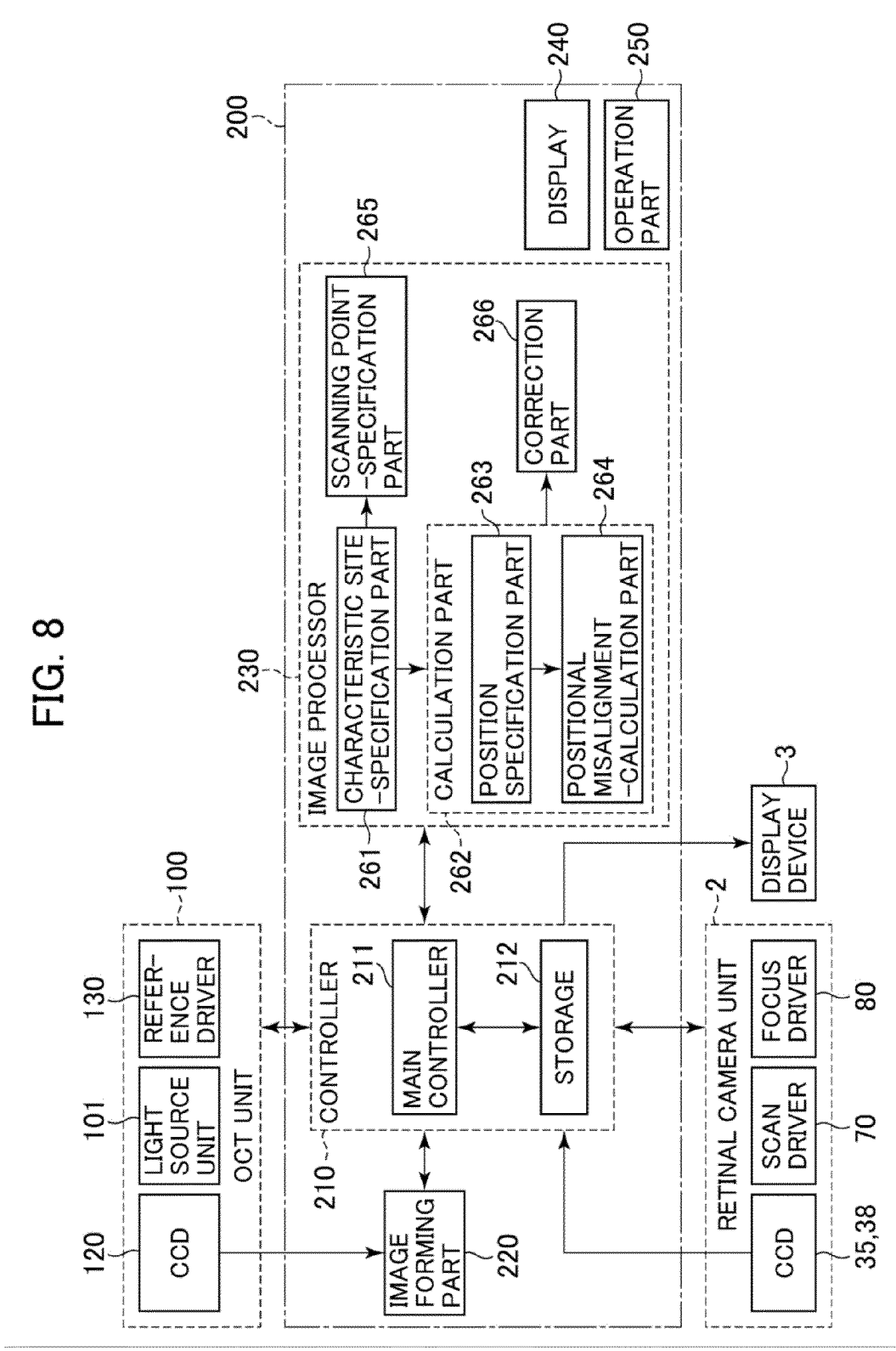
FIG. 8 is a schematic block diagram showing an example of a configuration of an embodiment of a fundus observation apparatus according to the present invention.

The configuration of the control system of the fundus observation apparatus is described. The control system of the fundus observation apparatus has parts in common with the first embodiment (ref. FIG. 3). One example of the configuration of the control system of the fundus observation apparatus is shown in FIG. 8. It should be noted that among the component elements shown in FIG. 8, the same symbols are given to those that are common in the first embodiment.

Configurations except for the image processor 230 are the same as the first embodiment. The image processor 230 has a characteristic site-specification part 261, calculation part 262, scanning point-specification part 265, and correction part 266. Hereinafter, the calculation process of the positional misalignment amount in the fundus surface direction and the calculation process of the positional misalignment amount in the depthwise direction of the fundus Ef are described separately.

The characteristic site-specification part 261 will be described. This fundus observation apparatus forms an observation image K (moving image) of the fundus Ef using the observation light source 11, the CCD image sensor 35 and so on. The observation image K is obtained by imaging the fundus Ef at a prescribed frame rate. The reciprocal of the frame rate corresponds to the "prescribed time interval" in the present invention.

Specifically, the fundus observation apparatus forms the observation image K by imaging the fundus Ef when the scanning with the signal light LS is executed. The configuration for forming the observation image K (the illumination optical system 10 and the imaging optical system 30) is one example of the "imaging part" in the present invention.

The characteristic site-specification part 261 analyzes each still image consisting of the observation image K and specifies an image region of a characteristic site of the fundus Ef. This process is described in the first embodiment. The characteristic site-specification part 261 is one example of the "image region-specifying part" in the present invention.

Furthermore, the characteristic site-specification part 261 obtains the position of an image region of a characteristic site in each still image as a position of the fundus Ef. That is, a two-dimensional coordinate system is preliminarily defined for each still image and the characteristic site-specification part 261 recognizes a coordinate value of the image region in the two-dimensional coordinate system as the position of the fundus Ef. Herein, as the coordinate value of the image region, for example, a coordinate value of a characteristic point (center point, point of gravity, etc.) within the image region may be used. It should be noted that because each still image is an image spreading in the fundus surface direction (xy-plane direction), the two-dimensional coordinate system and the xy-coordinate system are associated such that mutual coordinate conversion is possible. Specifically, the xy-coordinate system itself may be used as the two-dimensional coordinate system.

The imaging part and the image region-specifying part constitute one example of the "detection part" in the present invention.

Next, the calculation part 262 is described. The calculation part 262 calculates the positional misalignment amount of a plurality of A-scan images in the fundus surface direction, based on temporal changes in the position of the fundus Ef obtained by the characteristic site-specification part 261. The calculation part 262 constitutes one example of the "calculation part" along with the correction part 266 in the present invention. In order to execute the above process, the calculation part 262 has a position specification part 263 and a positional misalignment-calculation part 264.

Herein, the relation between the time interval for detecting the position of the fundus Ef (position detecting interval) and the scan time interval of a signal light LS is described. The scan time interval means the time interval from the time when the signal light LS is irradiated to one scanning point Rij until the signal light LS is irradiated to the next scanning point Ri(j+1).

It should be noted that a time interval (scanning line switching time) from the time when the signal light LS is irradiated to a final scanning point Rin of one scanning line Ri until the signal light LS is irradiated to the first scanning point R(i+1)1 of the next scanning line R(i+1) may be the same as the above scan time interval or it may also be different. If different, the position detecting interval may be controlled along with the scanning line switching time interval. Furthermore, instead of controlling the position detecting interval, the scanning line switching time interval may be set to a value that is an integral multiple of the scan time interval.

In this embodiment, a position detecting interval is set to an integral ($Q \geq 1$) multiple of a scan time interval. That is, the fundus observation apparatus detects the position of the fundus Ef each time a Q number of scanning points are scanned while irradiating the signal light LS sequentially to a plurality of scanning points Rij.

As a specific example, in case $Q=1$, the fundus observation apparatus detects the position of the fundus Ef each time when the signal light LS is irradiated to each scanning point Rij. Moreover, in case $Q=2$, the fundus observation apparatus detects the position of the fundus Ef each time two scanning points are scanned (that is, every other scanning point). Furthermore, the case when $Q=n$ (the number of scanning points on one scanning line Ri) corresponds to the first embodiment.

In general, the fundus observation apparatus detects the position of the fundus Ef every Q number of scanning points. Such action is realized by synchronizing control of the accumulated time of the CCD image sensor 35 and the control of the scan driver 70.

While such control is being executed, the calculation part 262 divides a plurality of A-scan images that have been sequentially formed into groups of A-scan images, wherein each group includes Q number of A-scan images. The "division" may actually be dividing the plurality of A-scan images for every Q number of the same (for example, each group of A-scan images are stored separately) or each group of A-scan images are made identifiable by adding an identification information, etc. In any case, it is sufficient as long as processes are executable with the individual group of A-scan images in the following processes. Consequently, a case in which the ratio (Q) of the position detecting interval and the scan time interval are stored and the plurality of A-scan images are processed for every Q number of the same in the following process, is included as the "division." Due to the above process, a group of Q number of A-scan images, a group of Q number of scanning points, and one detection result of the position of the fundus Ef are associated.

The position specification part 263 specifies the position of each 1-dimensional image group, based on the detection result of the position of the fundus Ef when Q number of scanning points corresponding to each group of A-scan images are being scanned. This process is described in further detail. That is, as described previously, because a group of scanning points and the detection result of the position of the fundus Ef are associated with a group of A-scan images, the position specification part 263 specifies, with reference to the association, the detection results of the position of the fundus Ef corresponding to each group of A-scan images so as to be regarded as the position of the group of A-scan images. This process corresponds to specifying the actual irradiation position Tij shown in FIG. 7B.

The positional misalignment-calculation part 264 calculates the positional misalignment amount based on the position of each group of A-scan images specified by the position specification part 263. The positional misalignment amount corresponds to the displacement between the scanning points Rij and the irradiation position Tij shown in FIG. 7B. It should be noted that in case $Q=1$, the positional misalignment amount may be accurately obtained with regard to each A-scan image. On the other hand, in case $Q \geq 2$, the positional misalignment amount may be accurately obtained for a certain A-scan image (that is, an A-scan image corresponding to the scanning point scanned at a moment when the position of the fundus Ef is detected) included in a group of A-scan images, but for other A-scan images, there will generally be some marginal errors.

The process of calculating the positional misalignment amount is described in further detail. The positional misalignment-calculation part 264 stores the positional information of each scanning point Rij (scanning point positional information) according to a preliminarily set scanning mode.

The scanning point positional information is represented by, for example, a coordinate value that is defined by the aforementioned xy-coordinate system. As another example, the scanning point positional information may also be represented by a coordinate value defined by a 2-dimensional coordinate system in which one of a plurality of scanning points Rij (for example, the first scanning point R11) is the origin. Furthermore, as scanning point positional information, an xy-coordinate value of one of the plurality of scanning points Rij (for example, the first scanning point R11) as well as an interval of adjacent scanning points (interval in the x-direction and/or interval in the y-direction) may also be stored. Moreover, instead of an interval of scanning points, the length of each scanning line, an interval of adjacent scanning lines, and a number of scanning points on each scanning line may also be stored. In any case, the form of the scanning point positional information may be arbitrary as long as the position of each scanning point is uniquely defined.

The positional misalignment-calculation part 264 first acquires a corresponding position (that is, an original position of each A-scan image) of each scanning point Rij with regard to each group of A-scan images from the scanning point positional information. Next, with regard to each group of A-scan images, the positional misalignment-calculation part 264 compares, for each scanning point Rij, the position of the acquired scanning point Rij and the actual irradiation position Tij specified by the position specification part 263. Thereby, the positional misalignment amount of the irradiation position Tij with respect to the position of the scanning point Rij is obtained.

Next, the correction part 266 is described. The correction part 266 corrects the position of the A-scan image in the fundus surface direction, based on the positional misalignment amount calculated by the positional misalignment-calculation part 264. The correction part 266 is one example of the "first correction part" in the present invention.

The process for correcting the position of the A-scan image is described in further detail. As described previously, the positional misalignment amount in the fundus surface direction obtained by the positional misalignment-calculation part 264 corresponds to the positional misalignment amount of the irradiation position Tij with respect to the position of the scanning point Rij. With regard to each A-scan image, the correction part 266 corrects the position of the A-scan image so as to cancel the corresponding positional misalignment amount, that is, so as to move the actual irradiation position Tij to the original position of the scanning point Rij. Consequently, an actually obtained A-scan image may be arranged in the original position (the position of the scanning point Rij). This is the end of the description regarding the calculation process of the positional misalignment amount in the fundus surface direction.

Subsequently, the calculation process of the positional misalignment amount in the depthwise direction of the fundus Ef is described. This calculation process is executed as in the first embodiment. That is, the calculation part 262 calculates the depthwise positional misalignment amount of a plurality of A-scan images, based on a group of 1-dimensional images (a separate group of A-scan images) based on the detection results of interference light LC comprising signal light LS separately scanned from the above scanning (scanning for obtaining the plurality of A-scan images, referred to as a main scanning) and reference light LR.

A separate group of A-scan images comprises a prescribed number of A-scan images arranged in the direction of the above separate scanning. The direction of the separate scanning is different from that of the main scanning. That is, a scanning line linking the prescribed number of scanning points in the separate scanning is presumed to cross each scanning line in the main scanning.

Prior to the calculation process of the positional misalignment amount in the fundus depth direction, the fundus observation apparatus forms separate groups of A-scan images by executing the above separate scanning and, furthermore, a tomographic image (standard tomographic image) corresponding to the scanning line in the separate scanning is formed, based on these separate groups of A-scan images.

As in the first embodiment, the calculation part 262 specifies an image region of a characteristic layer of the fundus Ef in the standard tomographic image, and specifies an image region of the characteristic layer in the tomographic image that is obtained in the main scanning.

Subsequently, as in the first embodiment, the calculation part 262 (positional misalignment-calculation part 264) calculates the depthwise displacement between the image region specified from the standard tomographic image and the image region specified from the tomographic image of the main scanning. Furthermore, as in the first embodiment, the calculation part 262 (positional misalignment-calculation part 264) calculates the depthwise positional misalignment amount of the A-scan image obtained in the main scanning, based on the calculated displacement.

The correction part 266 corrects the depthwise position of the A-scan image obtained in the main scanning, based on the depthwise positional misalignment amount calculated by the calculation part 262. This process is executed by moving, in the depthwise direction, the depthwise position of the A-scan image obtained from the main scanning so as to cancel the positional misalignment amount. The correction part 266 is one example of the "second correction part" in the present invention. This is the end of the description of the calculation process of the depthwise positional misalignment.

Next, the scanning point-specification part 265 is described. The scanning point-specification part 265 acts when there exists a still image (frame of an observation image K) for which an image region for a purpose is not specified by the characteristic site-specification part 261. The scanning point specification part 265 specifies the scanning point of an A-scan image corresponding to a still image with regard to each still image for which the image region is not specified. This process may be easily executed based on the aforementioned association of a group of A-scan images, a group of scanning points, and the detection results of the position of the fundus Ef, in addition to association of the detection results of the position of the fundus Ef and a still image (note that the detection of the position is executed based on a still image). The scanning point-specification part 265 is one example of the "scanning point-specifying part" in the present invention.

Once the scanning point is specified by the scanning point-specification part 265, the main controller 211 controls the scan driver and arranges the Galvano mirrors 43 and 44 in a position corresponding to the specified scanning point. Furthermore, the main controller 211 illuminates the observation light source 11 to capture the observation image K, and outputs low coherence light L0 by controlling the light source unit 101. Consequently, the signal light LS is irradiated to the specified scanning point. It should be noted that when a plurality of specified scanning points are present, these scanning points are sequentially scanned with the signal light LS.

The image forming part 220 receives, from the CCD image sensor 120, the detection results of interference light LC comprising the signal light LS and reference light LR, and forms a new A-scan image corresponding to the scanning point.

The image processor 230 executes the previously described process with respect to the new A-scan image and a corresponding still image (frame of the observation image K). Furthermore, the image forming part 220 is capable of forming a tomographic image of the fundus Ef, based on the new A-scan image and other scanning points that have already been obtained.

[Actions and Effects]

The actions and effects of the fundus observation apparatus 1 as described above will be described.

According to the fundus observation apparatus, the position of the fundus Ef may be detected at a prescribed time interval while scanning with the signal light LS the plurality of scanning points Rij, and the positional misalignment amount of a plurality of A-scan images in the fundus surface direction may be calculated based on temporal changes in the detected position of the fundus Ef. Furthermore, according to the fundus observation apparatus, it is possible to correct the position of the plurality of A-scan images based on the calculated positional misalignment amount.

Consequently, even if the eye E moves or blinks during scanning with the signal light LS, highly accurate OCT images may be obtained. Specifically, because the positions may be corrected by each group comprising a prescribed number (more than one) of A-scan images, more precise corrections than the first embodiment, in which the correction is executed for each tomographic image as a unit, are possible.

Furthermore, according to the fundus observation apparatus, when an image region of a characteristic site for obtaining the positional misalignment amount of an A-scan image is not specified, by specifying a scanning point corresponding to the A-scan image and remeasuring the scanning point, a new A-scan image may be formed. Consequently, even in the event of failing to obtain the positional misalignment amount, reobtaining may automatically be conducted; hence, making it possible to obtain highly accurate OCT images. Specifically, because only a scanning point corresponding to the A-scan image for which the positional misalignment amount failed to be obtained is remeasured, the examination time as well as the load on a patient may be reduced.

Furthermore, according to the fundus observation apparatus, a positional misalignment amount, in the depthwise direction of the fundus Ef, a plurality of A-scan images may be calculated, based on a separate group of A-scan images based on the detection results of interference light LC of the separately scanned signal light LS and reference light LR. Moreover, according to the fundus observation apparatus, the depthwise position of the plurality of A-scan images may be corrected based on the positional misalignment amount.

Consequently, even if the eye E moves or blinks while scanning with the signal light LS, highly accurate OCT images may be obtained. Specifically, because the depthwise position may be corrected by each group comprising a prescribed number of A-scan images, more precise corrections than the first embodiment, in which the correction is made for each tomographic image as a unit, are possible.

MODIFICATION EXAMPLE

Various modification examples related to the embodiments are described.

Modification Example 1

If the position detecting interval is greater than twice the scan time interval (Q≥2), the positional misalignment amount is obtained with respect to a group of Q number of A-scan images. In this modification example, the process of obtaining the amount of a plurality (less than Q) of positional misalignments with respect to a group of Q number of A-scan images, is described.

The positional misalignment-calculation part 264 obtains the detection results of the position of a fundus Ef while Q number of scanning points corresponding to a first group of A-scan images are being scanned and the detection results of the position of the fundus Ef while Q number of scanning points corresponding to the next second group of A-scan images are being scanned. The positional misalignment-calculation part 264 estimates the positional misalignment amount of each A-scan image included in the first group of A-scan images and/or the second group of A-scan images based on these two detection results.

Figure 9:
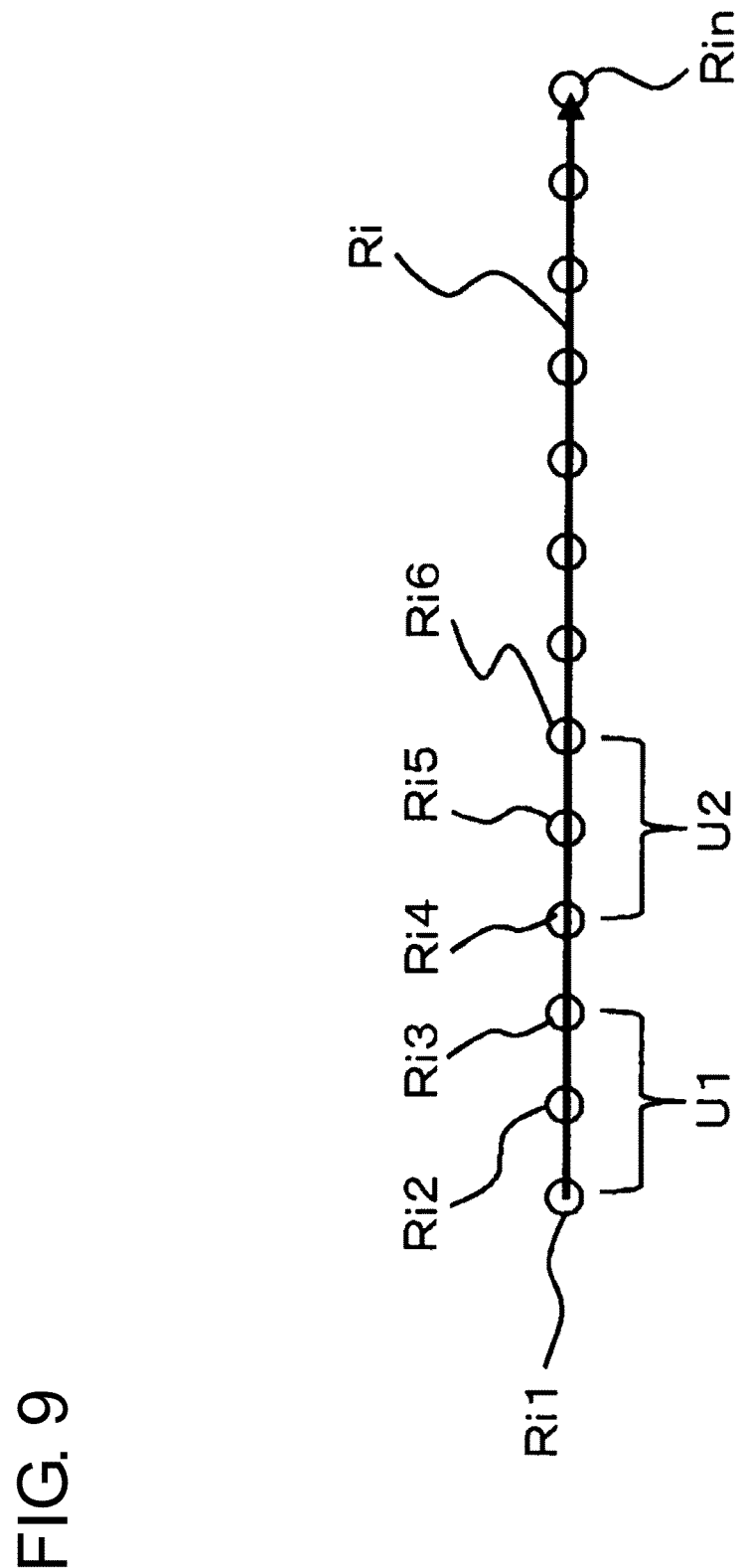
FIG. 9 is a schematic view for explaining a processing that estimates positional misalignment of 1-dimensional images (A-scan images) executed by a modification example of an embodiment of a fundus observation apparatus according to the present invention.

A specific example of this estimating process is described with reference to FIG. 9. In this specific example, Q=3. A first group of scanning points U1 corresponding to the first group of A-scan images includes three scanning points Ri1 to Ri3, and a second group of scanning points U2 corresponding to the second group of A-scan images includes three scanning points Ri4 to Ri6.

Presumably, the position of the fundus Ef at the time when the first scanning points Ri1 and Ri4 are being scanned is detected in each group of scanning points U1 and U2. That is, the image processor 230 obtains the positional misalignment amount corresponding to each group of scanning points U1 and U2, based on still images (frames of the observation image K) imaged when the first scanning points Ri1 and Ri4 in each group of scanning points U1 and U2 are being scanned. This process is described previously.

Herein, the positional misalignment amount corresponding to the first group of scanning points U1 is ($\Delta$x1, $\Delta$y1), and the positional misalignment amount corresponding to the second group of scanning points U2 is ($\Delta$x2, $\Delta$y2). The positional misalignment-calculation part 264 presumes that the positional misalignment amount of the first scanning points Ri1 and Ri4 are respectively ($\Delta$x1, $\Delta$y1) and ($\Delta$x2, $\Delta$y2).

Furthermore, the positional misalignment-calculation part 264 estimates the positional misalignment amount of each scanning point Ri2 and Ri3 sandwiched by two scanning points Ri1 and Ri4 in the following way, based on the positional misalignment amount ($\Delta$x1, $\Delta$y1) and ($\Delta$x2, $\Delta$y2).

Because the scan time interval is extremely short, the moving speed of the fundus Ef from the time when the scanning point Ri1 is scanned until the scanning point Ri4 is scanned may be assumed to be at a constant speed. Moreover, each scanning point Ri2 and Ri3 subject to the estimation is respectively located at a point where the line linking the scanning points Ri1 and Ri4 is internally divided into 1:2 and 2:1.

Under the above conditions, the positional misalignment-calculation part 264 calculates (($\Delta$x2−$\Delta$x1)/3, ($\Delta$y2−$\Delta$y1)/3), and the calculation result is regarded as the positional misalignment amount corresponding to the scanning point Ri2. At the same time, (2×($\Delta$x2−$\Delta$x1)/3, 2×($\Delta$y2−$\Delta$y1)/3) is calculated by the positional misalignment-calculation part 264, and this is regarded as the positional misalignment amount corresponding to the scanning point Ri3. In this way, the positional misalignment amount corresponding to each of the four scanning points Ri1 to Ri4 is obtained.

It should be noted that the positional misalignment amount corresponding to each scanning point Ri5 and Ri6 is obtained in the same way with reference to the positional misalignment amount corresponding to the next group of scanning points following the second group of scanning points U2. In this fashion, the positional misalignment-calculation part 264 sequentially obtains a positional misalignment amount corresponding to each scanning point Rij.

Thus far, with the first scanning points Ri1 and Ri4 of the groups of scanning points U1 and U2 being standard, the positional misalignment amounts corresponding to the scanning points Ri2 and Ri3 sandwiched by them are estimated, but even if other scanning points are regarded as standard, the positional misalignment amount corresponding to each scanning point sandwiched by the standard two scanning points may be likewise estimated. For example, if scanning points Ri2 and Ri5 in the middle are regarded as standard, it is possible to estimate the positional misalignment amounts corresponding to the scanning point Ri3 in the first group of scanning points U1 and the scanning point Ri4 in the second group of scanning points U2. Moreover, if the last scanning points Ri3 and Ri6 are regarded as standard, it is possible to estimate the positional misalignment amounts corresponding to scanning points Ri4 and Ri5 in the second group of scanning points U2.

The correction part 266 may correct the position of each of a plurality of A-scan images, based on the obtained positional misalignment amount.

According to this modification example, the positional misalignment amount for each A-scan image may be obtained while detecting the position of the fundus Ef for every Q number of scanning points. Therefore, even if there are restrictions on the detection interval of the position of the fundus Ef, the positional misalignment amount of each A-scan image may be obtained. Furthermore, there is an advantage in making it possible to set a short scan time interval.

Modification Example 2

In the above embodiment, the position of an already formed A-scan image is corrected, based on the positional misalignment amount of the A-scan image. On the other hand, in this modification example, an invention for controlling scanning with a signal light LS based on the positional misalignment amount of an A-scan image in real time is described.

During scanning with the signal light LS, the image processor 230 sequentially calculates the positional misalignment amount based on the position of a fundus Ef that is sequentially detected at a prescribed time interval. The detection of the position of the fundus Ef may be carried out in the same way as in the above embodiment. Furthermore, the process of calculating each positional misalignment amount is also executed as in the above embodiment.

The main controller 211 controls the scan driver 70 based on the positional misalignment amount that is sequentially calculated and corrects the irradiation position of the signal light LS with respect to the fundus Ef. The main controller 211 is one example of the "controlling part" in the present invention.

The correction process of the irradiation position of the signal light LS is described in further detail. The position of the Galvano mirrors 43 and 44 (mirror position) with respect to each scanning point Rij is preliminarily set based on a scanning mode that is executed. The main controller 211 controls the scan driver 70 and sequentially moves the Galvano mirrors 43 and 44 to each mirror position following the scanning sequence of the scanning point Rij.

However, if the eye E moves during measurement, the signal light LS ends up being irradiated to a place outside the original position of the scanning point Rij, that is, outside the original measuring position. In the above embodiment, the positional misalignment caused this way is amended by correcting the position of an already obtained A-scan image.

On the other hand, in this modification example, the irradiation position of the signal light LS is corrected according to the calculated positional misalignment amount. That is, the main controller 211 controls the scan driver 70 so as to irradiate the signal light LS to a position displaced by the relevant positional misalignment amount from the original position of the next scanning point Rij.

By sequentially executing this process, the irradiation position of the signal light LS may follow the movement of the eye E (fundus Ef); thereby, making it possible to obtain highly accurate OCT images even if the eye E moves during scanning with the signal light LS.

Modification Example 3

Figure 10:
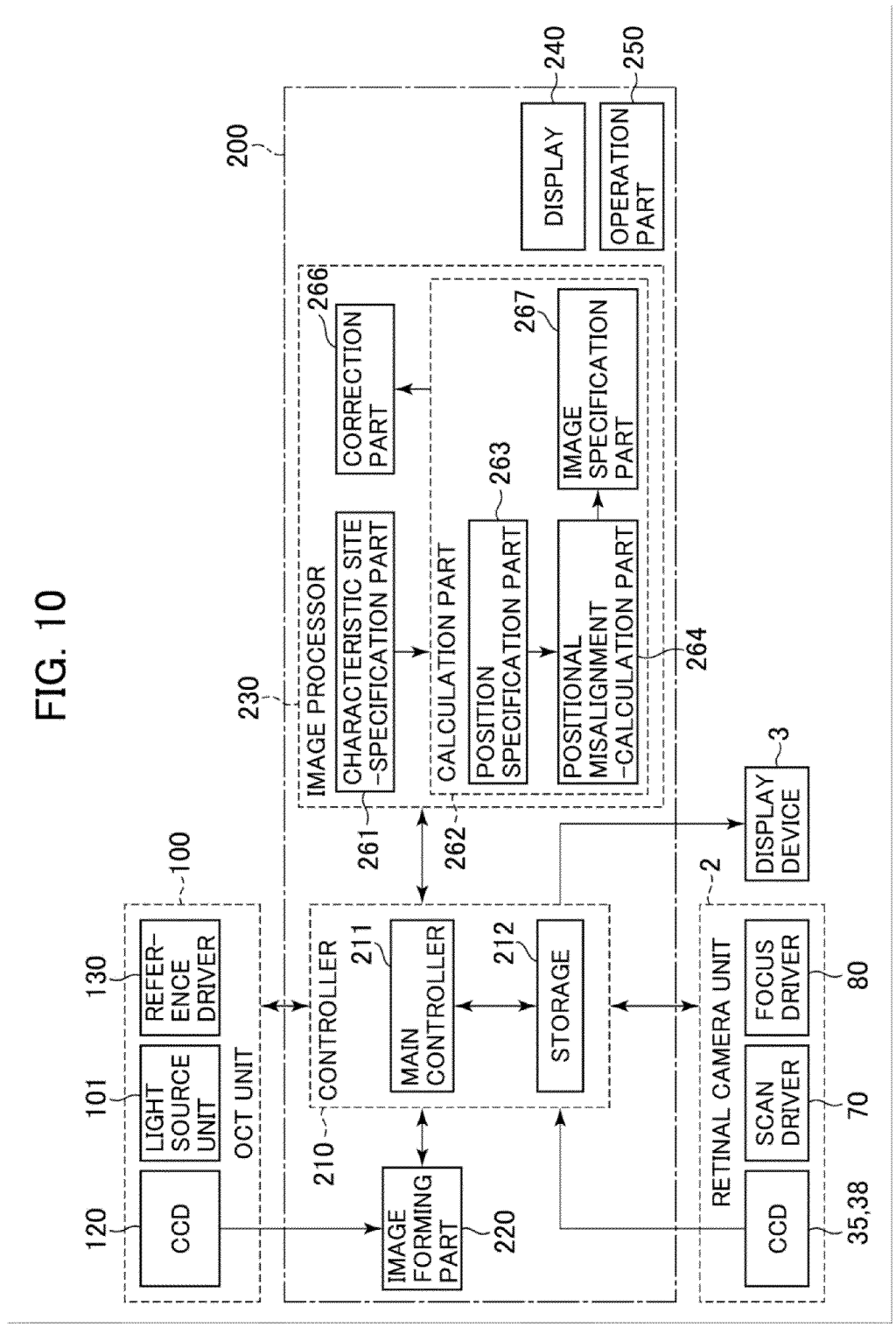
FIG. 10 is a schematic block diagram showing an example of a configuration of a modification example of an embodiment of a fundus observation apparatus according to the present invention.

In this modification example, an invention in which remeasurement is executed if positional misalignment is significant is described with reference to FIG. 10.

The calculation part 262 is provided with an image specification part 267. The image specification part 267 compares, with a prescribed value, each positional misalignment amount calculated by the positional misalignment-calculation part 264. Further, the image specification part 267 specifies an A-scan image with a positional misalignment amount that is equal to or greater than the prescribed value. The image specification part 267 is one example of the "image specifying part" of the present invention.

The main controller 211 controls the light source unit 101 and scan driver 70 to reirradiate the signal light LS toward a scanning point corresponding to the specified A-scan image. If more than two A-scan images are specified, the main controller 211 sequentially reirradiates the signal light LS towards the two or more corresponding scanning points.

Based on the detection results of the interference light LS of the reirradiated signal light LS and reference light LR, the image forming part 220 forms a new A-scan image at the scanning point. The image forming part 220 may form a tomographic image based on the new A-scan image and A-scan images corresponding to other scanning points.

According to this modification example, because remeasurement of a scanning point corresponding to an A-scan image with a significant positional misalignment may be automatically executed, even if the eye E moves significantly during the measurement, it is possible to obtain highly accurate OCT images by automatically remeasuring the same. Furthermore, even if the eye E blinks during the measurement, it becomes impossible to calculate the positional misalignment amount (it is determined that the positional misalignment amount at that time is equal to or greater than a prescribed value) and rescanning takes place; hence, highly accurate OCT images may be obtained.

Modification Example 4

Figure 11:
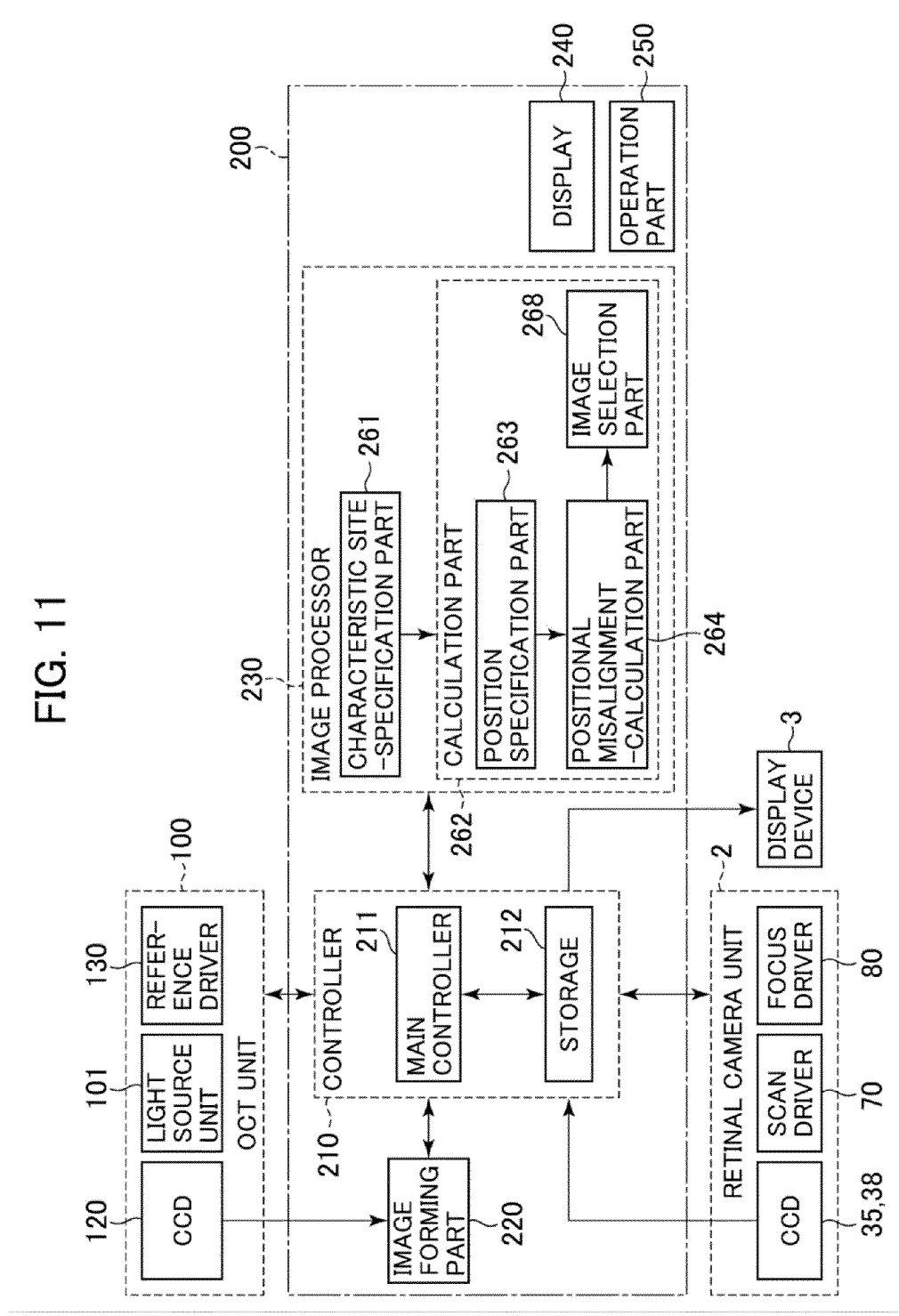
FIG. 11 is a schematic block diagram showing an example of a configuration of a modification example of an embodiment of a fundus observation apparatus according to the present invention.

In this modification example, an invention for selectively arranging A-scan images according to the position of scanning points is described with reference to FIG. 11.

An image selection part 268 is provided with an image selection part 268. Based on the positional misalignment amount calculated by the positional misalignment-calculation part 264, with regard to each scanning point Rij, the image selection part 268 selects the A-scan image closest to the original position of the scanning point Rij among the plurality of A-scan images that have been obtained.

This process is described in more detail. As described previously, the original position of each scanning point Rij is preliminarily set. On the other hand, the position of each A-scan image is obtained based on the position of a corresponding scanning point Rij and a calculated positional misalignment amount. In other words, the image selection part 268 regards the position which is the position of the scanning point Rij displaced by the positional misalignment amount as the position of the A-scan image.

Furthermore, with regard to each scanning point Rij, the image selection part 268 selects the A-scan image closest to the original position of the scanning point Rij. It should be noted that if the positional misalignment amount is small enough, an A-scan image corresponding to the scanning line Rij is selected, but if the positional misalignment amount is great, other A-scan images might be selected. The image selection part 268 is one example of the "image selecting part" in the present invention.

The image forming part 220 forms a tomographic image by arranging the selected A-scan image with respect to each scanning point Rij according to the arrangement of a plurality of scanning points.

According to this modification example, a tomographic image may be formed by selecting the A-scan image that is closest to each scanning point Rij; thereby, making it possible to obtain highly accurate OCT images without performing further scanning.

Modification Example 5

There are other utilization methods of the positional misalignment amount of an A-scan image in addition to correcting the position of the A-scan image. In this modification example, one example of a utilization method other than the positional correction is described.

In this modification example, the positional misalignment amount is used in a process of superposing a plurality of tomographic images based on a plurality of scans performed along the same scanning line. This superposing process is for the purpose of achieving high quality images.

In this modification example, as previously described, scanning with the signal light LS is performed along a prescribed scanning line. As a scanning mode at this time, for example, radial scanning or circle scanning is applied. This fundus observation apparatus repeatedly performs scanning with the signal light LS along a prescribed scanning line. The image forming part 220 repeatedly forms a plurality of A-scan images corresponding to a plurality of scanning points on the scanning line according to the repetitive scanning. Consequently, a tomographic image from each scanning is obtained. The positional misalignment-calculation part 264 repeatedly calculates the positional misalignment amount of A-scan images that are repeatedly formed.

Figure 12:
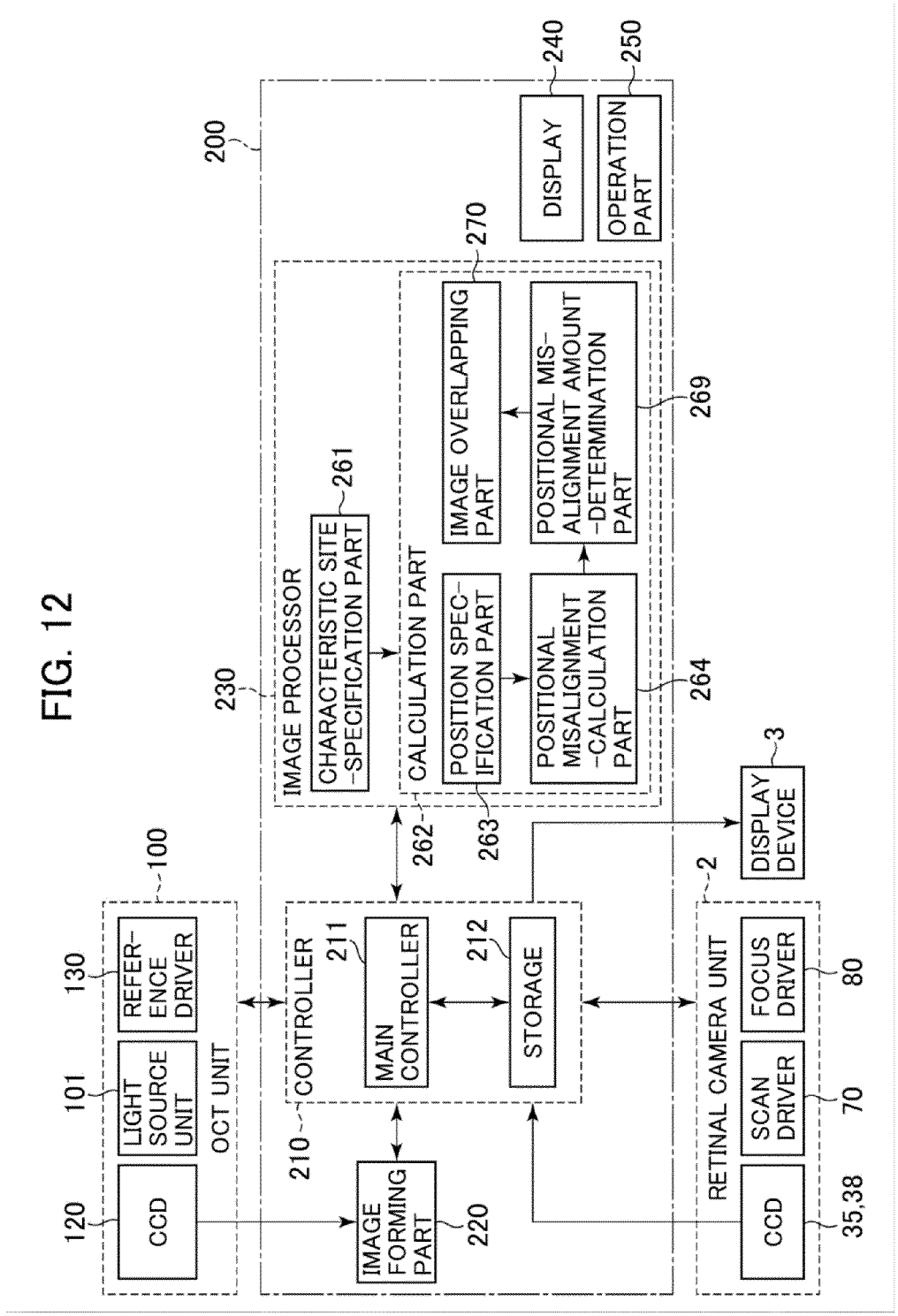
FIG. 12 is a schematic block diagram showing an example of a configuration of a modification example of an embodiment of a fundus observation apparatus according to the present invention.

As shown in FIG. 12, the calculation part 262 is provided with a positional misalignment amount-determination part 269 and an image overlapping part 270. The positional misalignment amount-determination part 269 determines whether or not each positional misalignment amount repeatedly calculated by the positional misalignment-calculation part 264 is included in a prescribed permissible range. As the permissible range, a range with a smaller positional misalignment amount than the prescribed value is preliminarily set. The positional misalignment amount-determination part 269 is one example of the "determination part" in the present invention.

The image overlapping part 270 superposes a set of A-scan images whose positional misalignment amount is determined to be included within the prescribed permissible range. To do this, the image overlapping part 270 forms a set of A-scan images corresponding to each scanning point Rij and overlaps each set of A-scan images. The image overlapping part 270 is one example of the "image overlapping part" in the present invention.

The image forming part 220 arranges a plurality of new A-scan images formed by this overlapping process according to the arrangement of a plurality of scanning points Rij. Consequently, a tomographic image along a prescribed scanning line is formed.

According to this modification example, only A-scan images accommodated within the permissible range of the positional misalignment amount may be overlapped; hence, making it possible to easily obtain high quality images. It should be noted that in case of having an insufficient number of A-scan images to be overlapped, scanning is performed again as in three-dimensional scanning.

Other Modification Examples

In the above embodiments, the position of the fundus Ef is detected based on the observation image K, but the detection part in the present invention is not limited to this. As long as the detection part is capable of detecting the position of the fundus Ef at a prescribed time interval during scanning with the signal light LS, an arbitrary configuration is applicable.

For example, a method cited in the following literature may be used: "Image stabilization for scanning laser ophthalmoscopy", Daniel X. Hammer and three others, 30 Dec. 2002/ Vol. 10, No. 26/OPTICS EXPRESS 1542.

The configuration cited in the literature includes a confocal tracking reflectometer, dither scanner, and tracking galvanometers.

A tracking beam tracks down the characteristic point of a fundus. The confocal tracking reflectometer is used so that movement of the eye can be determined by the reflection light of the beam irradiated to the fundus. The beam drives the dither scanner, with a prescribed resonant frequency (8 kHz) and adding 90 degrees of phase difference between the x and y scanners, in a manner such that a circle is drawn by the beam. When the beam is irradiated to the characteristic point, the detection signal includes the signal of the above resonant frequency, and the phase is proportional to the distance between the beam and a target. Detection of phase sensitivity using a lock-in amplifier generates an error signal, which is applied to a DSP feed back control loop. The control loop provides instructions to the tracking Galvanometer according to the processed error signal so that images are locked in response to the movement of the eye.

The above embodiments or modification examples may be realized using the detection results of the movement of the fundus obtained by the fundus tracking which is realized by this configuration.

In the above embodiment, the position of the reference mirror 114 is changed so as to change an optical path length difference between the optical path of the signal light LS and the optical path of the reference light LR. However, a method for changing the optical path length difference is not limited thereto. For example, it is possible to change the optical path length difference by moving the retinal camera unit 2 and the OCT unit 100 with respect to the eye E to change the optical path length of the signal light LS. In a case that an object is not a living site or the like, it is also effective to change the optical path length difference by moving the object in the depth direction (z-direction).

The computer program used in the above embodiments can be stored in any kind of recording medium that can be read by a drive device of a computer. As this recording medium, for example, an optical disk, a magneto-optic disk (CD-ROM, DVD-RAM, DVD-ROM, MO, and so on), and a magnetic storing medium (a hard disk, a floppy Disk™, ZIP, and so on) can be used. Moreover, it is possible to store into a storing device such as a hard disk drive and a memory. Besides, it is possible to transmit/receive this program through a network such as the internet and a LAN.

The configuration described above is merely one example for favorably implementing the present invention. Therefore, it is possible to properly make arbitrary modification within the scope of the present invention.

What is claimed is:

1. A fundus observation apparatus comprising:
   an optical system that splits light from a light source into signal light and reference light, generates interference light by superposing said signal light that has passed through the fundus of an eye and reference light that has passed through a reference optical path, and detects the generated interference light;
   a scanning part that sequentially irradiates said signal light to a plurality of scanning points by scanning said fundus with said signal light and;
   an image forming part that forms 1-dimensional images extending depthwise of said fundus at each of said plurality of scanning points based on the detection results of said interference light by said optical system;
   a detection part that detects the position of said fundus at a prescribed time interval when scanning with said signal light; and
   a calculation part that calculates the positional misalignment amount for each 1-dimensional image in the fundus surface direction, based on temporal changes of said detected position of said fundus for each 1-dimensional image, wherein
   the image forming part is configured to form a tomographic image by respectively arranging a plurality of the 1-dimensional images according to an arrangement of the plurality of scanning points.

2. The fundus observation apparatus according to claim 1, wherein
   said prescribed time interval is a substantially integral multiple of a scan time interval that is from the timing at which said signal light is irradiated to one of said plurality of scanning points to the timing at which said signal light is irradiated to the next scanning point;
   while said signal light is sequentially irradiated to said plurality of scanning points by said scanning part, said detection part detects the position of said fundus each time when the relevant integral number of scanning points are scanned; and said calculation part divides said plurality of 1-dimensional images into 1-dimensional image groups, each group comprising the relevant integral number of 1-dimensional images, specifies the position of each 1-dimensional image group based on the detection results of the position of said fundus when the relevant integral number of scanning points corresponding to each 1-dimensional image group are being scanned, and calculates said positional misalignment amount based on said specified position of each 1-dimensional image group.

3. The fundus observation apparatus according to claim 2, wherein said integral is one;

said 1-dimensional image group consists of one 1-dimensional image; and said calculation part specifies the position of the 1-dimensional image with regard to said plurality of 1-dimensional images based on the detection results of the position of said fundus when a scanning point corresponding to the 1-dimensional image is being scanned, and calculates said positional misalignment amount based on the specified plurality of positions.

4. The fundus observation apparatus according to claim 2, wherein said integral is equal to or greater than two;

said 1-dimensional image group consists of two or more 1-dimensional images; and said calculation part estimates, based on the detection results of the position of said fundus when two or more scanning points corresponding to one of said plurality of 1-dimensional image groups are being scanned and the detection results of the position of said fundus when two or more scanning points corresponding to the next 1-dimensional image group are being scanned, said positional misalignment amount of a 1-dimensional image included in said one of said plurality of 1-dimensional image group and/or said next 1-dimensional image group.

5. The fundus observation apparatus according to claim 1, wherein said detection part includes an imaging part that forms a moving image by imaging said fundus at said prescribed time interval when the scanning with said signal light is executed by said scanning part, and an image region-specifying part that specifies an image region of a characteristic site of said fundus in each still image forming said moving image, and obtains the position of said image region in said each still image as the position of said fundus.

6. The fundus observation apparatus according to claim 5, wherein said calculation part includes a scanning point-specifying part that, when there is a still image in which said image region is not specified by said image region-specifying part, specifies a scanning point of a 1-dimensional image corresponding to the still image;

said scanning part reirradiates said signal light to the specified scanning point; and said image forming part forms a new 1-dimensional image based on the detection results of interference light of said reirradiated signal light and said reference light.

7. The fundus observation apparatus according to claim 1, wherein said calculation part includes a first correction part that corrects the position of said plurality of 1-dimensional images in the fundus surface direction, based on said calculated positional misalignment amount.

8. The fundus observation apparatus according to claim 1, wherein said calculation part sequentially calculates said positional misalignment amount based on the position of said fundus that is sequentially detected at said prescribed time interval when scanning with said signal light is executed; and comprising a controlling part that corrects the irradiation position of said signal light to said fundus by controlling said scanning part based on said sequentially calculated positional misalignment amount.

9. The fundus observation apparatus according to claim 1, wherein, said plurality of scanning points are arranged along a prescribed scanning line;

said scanning part repeatedly scans along said prescribed scanning line with said signal light;

said image forming part repeatedly forms said plurality of 1-dimensional images corresponding to said plurality of scanning points following the repetitive scanning;

said calculation part repeatedly calculates said positional misalignment amount following the repetitive formations;

comprising:

a determination part which determines whether or not the repeatedly calculated each positional misalignment amount is included in a prescribed permissible range; and an image overlapping part that overlaps, for each 1-dimensional image corresponding to each scanning point, a set of said plurality of 1-dimensional images corresponding to said positional misalignment amount determined as inclusive to said prescribed permissible range; and said image forming part forms a tomographic image along said prescribed scanning line by arranging a plurality of new 1-dimensional images formed as a result of said overlapping in accordance with the arrangement of said plurality of scanning points.

10. The fundus observation apparatus according to claim 1, wherein said calculation part includes an image specifying part that specifies a 1-dimensional image with the calculated positional misalignment amount of greater than a prescribed value;

said scanning part reirradiates said signal light towards a scanning point corresponding to each 1-dimensional image specified by said image specifying part; and said image forming part forms a new 1-dimensional image at the scanning point based on the detection results of interference light of said reirradiated signal light and said reference light.

11. The fundus observation apparatus according to claim 1, wherein said plurality of scanning points are arranged along a prescribed scanning line;

said calculation part includes an image selecting part that, for each of said plurality of scanning points, selects the 1-dimensional image closest to the original position of the scanning point among said plurality of 1-dimensional images, based on the calculated positional misalignment amount; and said image forming part forms a tomographic image along said prescribed scanning line by arranging the selected 1-dimensional image in accordance with the arrangement of said plurality of scanning points.

12. The fundus observation apparatus according to claim 1, wherein
said calculation part calculates the positional misalignment amount of said plurality of 1-dimensional images in the depth direction of said fundus, based on a separate 1-dimensional image group arranged in a separate scanning direction that is formed by said image forming part based on the detection results of interference light of signal light that is separately scanned by said scanning part and reference light.

13. The fundus observation apparatus according to claim 12, wherein
said scanning part sequentially irradiates said signal light, as said separate scanning, to a prescribed number of scanning points along a scanning line crossing the arrangement direction of said plurality of scanning points;
said image forming part forms said 1-dimensional image at each of said prescribed number of scanning points and forms a tomographic image corresponding to said scanning line based on said prescribed number of formed 1-dimensional images; and
said calculation part specifies an image region of a characteristic layer of said fundus in said tomographic image, specifies the image region of said characteristic layer in a tomographic image formed by arranging said plurality of scanning points, calculates the depthwise displacement of said image region corresponding to said scanning line and said image region corresponding to said plurality of scanning points, and calculates the depthwise positional misalignment amount of said plurality of 1-dimensional images based on the calculated displacement.

14. The fundus observation apparatus according to claim 12, wherein
said calculation part includes a second correction part that corrects the position of said plurality of 1-dimensional images in the depth direction, based on the calculated depthwise positional misalignment amount.

15. A fundus observation apparatus comprising:
an optical system that splits low coherence light into signal light and reference light, generates interference light by superposing said signal light that has passed through the fundus of an eye and reference light that has passed through a reference optical path, and detects the generated interference light;
a scanning part that two-dimensionally scans said fundus with said signal light;
an image forming part that forms, based on the detection results of said interference light, a 3-dimensional image corresponding to the region of said fundus in which the two-dimensional scanning with said signal light is executed;
an imaging part that forms a moving image of said fundus when the two-dimensional scanning with said signal light is executed; and
a correction part that corrects the position of said 3-dimensional image in a fundus surface direction based on the formed moving image, and corrects the position of said 3-dimensional image in a fundus depth direction, based on a tomographic image of said fundus that is formed by said image forming part based on the detection results of interference light of separately scanned signal light by said scanning part and reference light, wherein said scanning part scans with said signal light along each of a plurality of scanning lines that are parallel to each other, as said two-dimensional scanning;
said image forming part forms a tomographic image corresponding to each of said plurality scanning lines and forms said 3-dimensional image based on the formed plurality of tomographic images;
said imaging part forms said moving image by forming still images when the scanning with said signal light is executed along each of said plurality of scanning lines; and
said correction part specifies an image region of a characteristic site of said fundus in each of said plurality of still images, calculates the positional misalignment amount of said image region in said plurality of still images, and corrects the position of said 3-dimensional image in the fundus surface direction by correcting the relative position of said plurality of tomographic images based on the calculated positional misalignment amount.

16. The fundus observation apparatus according to claim 15, wherein
said correction part calculates an interval of said plurality of tomographic images after said relative position is corrected; and
said image forming part forms a plurality of tomographic images arranged at equal intervals based on the calculated interval as well as said plurality of tomographic images, and forms a 3-dimensional image based on the tomographic images formed at equal intervals.

17. The fundus observation apparatus according to claim 15, wherein
said scanning part scans with said signal light along each of a plurality of scanning lines that are parallel to each other, as the two-dimensional scanning;
said image forming part forms a tomographic image corresponding to each of said plurality of scanning lines and forms said 3-dimensional image based on the formed plurality of tomographic images;
said imaging part forms said moving image by forming a still image when the scanning with said signal light is executed along each of said plurality of scanning lines;
said correction part specifies an image region of a characteristic site of said fundus in each of said plurality of still images, calculates the positional misalignment amount in said image region in said plurality of still images, and determines whether or not the calculated positional misalignment amount is equal to or greater than a prescribed value;
when determined that said positional misalignment amount is equal to or greater than the prescribed value, said scanning part rescans with said signal light along a scanning line located to a close region of a scanning line of a tomographic image corresponding to the still image whose positional misalignment amount is determined to be equal to or greater than the prescribed value; and
said image forming part forms a new tomographic image based on the detection results of interference light of the rescanned signal light and the reference light, and forms a 3-dimensional image corresponding to said close region based on said new tomographic image.

18. The fundus observation apparatus according to claim 17,
wherein said image forming part forms said 3-dimensional image based on a tomographic image corresponding to said still image whose positional misalignment amount is determined to be less than the prescribed value and said new tomographic image.

19. The fundus observation apparatus according to claim 15, wherein
said scanning part scans with said signal light along each of a plurality of scanning lines that are parallel to each other, as said two-dimensional scanning;
said image forming part forms a tomographic image corresponding to each of said plurality of scanning lines and forms said 3-dimensional image based on the formed plurality of tomographic images;
said imaging part forms said moving image by forming a still image when said the scanning with the signal light is executed along each of said plurality of scanning lines;
said correction part specifies an image region of a characteristic site of said fundus in each of said plurality of still images, calculates the positional misalignment amount of said image region in said plurality of still images, and selects, for each of said plurality of scanning lines, a tomographic image closest to the original position of the scanning line among said plurality of tomographic images based on the calculated positional misalignment amount; and
said image forming part forms said 3-dimensional image based on the selected tomographic image.

20. The fundus observation apparatus according to claim 15, wherein
when there exists said still image in which the image region of said characteristic site is not specified, said correction part specifies a scanning line of a tomographic image corresponding to the still image;
said scanning part rescans with said signal light along the specified scanning line; and
said image forming part forms a new tomographic image based on the detection results of interference light of the rescanned signal light and the reference light, and forms a 3-dimensional image of a region corresponding to the scanning line based on said new tomographic image.

21. The fundus observation apparatus according to claim 17, wherein
when there exists said still image in which the image region of said characteristic site is not specified, said correction part specifies a scanning line of a tomographic image corresponding to the still image;
said scanning part rescans with said signal light along the specified scanning line; and
said image forming part forms a new tomographic image based on the detection results of interference light of the rescanned signal light and the reference light, and forms a 3-dimensional image of a region corresponding to the scanning line based on said new tomographic image.

22. The fundus observation apparatus according to claim 19, wherein
when there exists said still image in which the image region of said characteristic site is not specified, said correction part specifies a scanning line of a tomographic image corresponding to the still image,
said scanning part rescans with said signal light along the specified scanning line, and
said image forming part forms a new tomographic image based on the detection results of interference light of the rescanned signal light and the reference light, and forms a 3-dimensional image of a region corresponding to the scanning line based on said new tomographic image.

23. The fundus observation apparatus according to claim 15, wherein
said image forming part forms a 3-dimensional image of said fundus based only on the center portion excluding an image region in the tomographic image corresponding to a prescribed end part region in each of said plurality of scanning lines.

24. The fundus observation apparatus according to claim 17, wherein
said image forming part forms a 3-dimensional image of said fundus based only on the center portion excluding an image region in the tomographic image corresponding to a prescribed end part region in each of said plurality of scanning lines.

25. The fundus observation apparatus according to claim 19, wherein
said image forming part forms a 3-dimensional image of said fundus based only on the center portion excluding an image region in the tomographic image corresponding to a prescribed end part region in each of said plurality of scanning lines.

26. The fundus observation apparatus according to claim 15, wherein
said scanning part scans with said signal light, as said separate scanning, along each of a prescribed number of scanning lines for correction crossing said plurality of scanning lines,
said image forming part forms a tomographic image for correction corresponding to each of said scanning lines for correction, and
said correction part specifies an image region of a characteristic layer of said fundus in said prescribed number of formed tomographic images for correction, and corrects the position of said 3-dimensional image in the fundus depth position by moving each of said plurality of tomographic images in the fundus depth position so as to match the depthwise position of the specified image region and the depthwise position of said image region of the characteristic layer in each of said plurality of tomographic images.

* * * * *

UNITED STATES PATENT AND TRADEMARK OFFICE
CERTIFICATE OF CORRECTION

Page 1 of 1

PATENT NO.       : 8,573,776 B2
APPLICATION NO.  : 13/264117
DATED            : November 5, 2013
INVENTOR(S)      : Hiroshi Koizumi et al.

It is certified that error appears in the above-identified patent and that said Letters Patent is hereby corrected as shown below:

In the Specification

Column 26, line 3, insert -- 70 -- between "drive" and "and".

Column 30, line 4, Start new paragraph with word "Modification".

Signed and Sealed this
Fourteenth Day of October, 2014

Michelle K. Lee
*Deputy Director of the United States Patent and Trademark Office*